United States Patent
Ma et al.

(10) Patent No.: US 8,071,533 B2
(45) Date of Patent: Dec. 6, 2011

(54) COMPOSITIONS AND METHODS FOR MODULATING STORE-OPERATED CALCIUM ENTRY

(75) Inventors: Jianjie Ma, Bellemead, NJ (US); Noah Weisleder, Elizabeth, NJ (US); Zui Pan, Piscataway, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 357 days.

(21) Appl. No.: 12/279,871

(22) PCT Filed: Mar. 20, 2007

(86) PCT No.: PCT/US2007/064365
§ 371 (c)(1),
(2), (4) Date: Feb. 11, 2009

(87) PCT Pub. No.: WO2007/109648
PCT Pub. Date: Sep. 27, 2007

(65) Prior Publication Data
US 2010/0061942 A1 Mar. 11, 2010

Related U.S. Application Data

(60) Provisional application No. 60/783,999, filed on Mar. 20, 2006.

(51) Int. Cl.
*C07K 14/00* (2006.01)
(52) U.S. Cl. .............................................. 514/1; 530/350
(58) Field of Classification Search ....... 514/1; 530/350
See application file for complete search history.

(56) References Cited

U.S. PATENT DOCUMENTS
2002/0111471 A1* 8/2002 Lo et al. ........................ 536/23.2

FOREIGN PATENT DOCUMENTS
WO    WO 00/31113    6/2000

OTHER PUBLICATIONS

Deshayes et al., "Insight into the mechanism of internalization of the cell-penetrating carrier peptide Pep-1 through conformational analysis", Biochemistry 2004 43:1449-1457.
Futaki, Shiroh, "Arginine-rich peptides:potential for intracellular delivery of macromolecules and the mystery of the translocation mechanisms", International Journal of Pharmaceutics 2002 245:1-7.
Hashida et al., "Fusion of HIV-1 Tat protein transduction domain to poly-lysine as a new DNA delivery tool", British Journal of Cancer 2004 90:1252-1258.
Ho et al., "Synthetic protein transduction domains:enhanced transduction potential in Vitro and in Vivo[1]", Cancer Research 2001 61:474-477.
Morris et al., "Peptide carrier for the delivery of biologically active proteins into mammalian cells", Nature Biotechnology 2001 19:1173-1176.
Schwartz et al., "Peptide-mediated cellular delivery", Current Opinion in Molecular Therapeutics 2000 2(2):162-167.
Wadia et al., "Transducible TAT-HA fusogenic peptide enhances escape of TAT-fusion proteins after lipid raft macropinocytosis", Nature Medicine 2004 10(3):310-315.
NCBI Accession No: NP_ 444308 [gi:16716357] with revision history—Nov. 1, 2001-Aug. 6, 2006.
Wadia et al., "Protein transduction technology", Current Opinion in Biotechnology 2002 13:52-56.

* cited by examiner

*Primary Examiner* — Karen Carlson
(74) *Attorney, Agent, or Firm* — Licata & Tyrrell P.C.

(57) ABSTRACT

Compositions and methods for modulating activity of store-operated calcium entry in cells or tissues are provided. The compositions comprise the P311 protein, fused to a cell-penetrating peptide and formulated for delivery to tissues and cells. This protein has been shown to increase the levels of store-operated calcium entry (SOCE) in gingival cells, skeletal muscle cells, and prostate epithelial cells. Also provided are methods for preventing and treating diseases that involve administration of the P311 fusion protein, as well as methods for increasing levels of SOCE in cells.

7 Claims, 15 Drawing Sheets

|  | 10 | 20 |
|---|---|---|
| hP311 | MVYYP-----ELFVWVSQEPFPN------KDMEGRLPKGRL | |
| mp311 | MVYYP-----ELLVWVSQEPFAY------KEMEGGLIKGRL | |
| 1DYWA | HRIIPNFMIQ---------GGDFTRGNGTGGESIYGE | |

|  | 30 | 40 | 50 | 60 | SEQ ID NO: |
|---|---|---|---|---|---|
| hP311 | PVPKEVNRKKNDETNAASLTPLGSSELRSPRISYLHPF | | | | 1 |
| mp311 | PVPKEVNRKKMEETGAASLTPPGSREFTSPATSYLHPF | | | | 10 |
| 1DYWA | KFPDENFKEKHTGPGVLSMANAGPNTNGSQFFLCTVKT | | | | 11 |

COMPOSITIONS AND METHODS FOR MODULATING STORE-OPERATED CALCIUM ENTRY

This patent application is a National Stage Application of International Application No. PCT/2007/064365 filed Mar. 20, 2007, which claims benefit of priority from U.S. Provisional Application Ser. No. 60/783,999, filed Mar. 20, 2006, teachings of which are herein incorporated by reference in their entirety.

BACKGROUND OF THE INVENTION

Calcium (Ca) ions act as a regulatory signal for a myriad of cellular processes, and disruption of calcium homeostasis within cells results in numerous pathological conditions. Ca is a messenger molecule in cell signaling that is released in response to numerous stimuli in nearly all cell types. Maintenance of intracellular Ca homeostasis is essential for effective cellular function and perturbation of Ca handling can result in cell death and tissue degeneration. Indeed, disruption of Ca homeostasis has been implicated in the pathogenesis of a variety of diseases including cancer, heart disease, diabetes and neurodegenerative disorders.

Two principal sources of Ca participate in regulating intracellular Ca homeostasis; a) the store of Ca located within sequestering organelles, primarily the endoplasmic reticulum (ER), and b) the vast reservoir of extracellular Ca. Ca stored within the ER is released in a controlled fashion through Ca channels, which are usually proteins from the Inositol 1,4,5-trisphosphate (IP3) receptor or ryanodine receptor (RyR) families. The Ca is then returned into the ER through the action of Ca pumps. The intracellular stores of Ca are replenished from the extracellular reservoir through store-operated Ca entry (SOCE). SOCE is a fairly ubiquitous phenomenon. It has been observed in operation in skeletal muscle (Pan, Z. et al. 2002. Nat. Cell. Biol. 4:379-383), in fibroblasts (Miyakawa, T. et al. 1998. Biochem. J. 329:107-114), and in epithelial cells (Vanden Abeele, F. et al. 2003. J. Biol. Chem. 278:15381-15389).

Gingivitis is an inflammatory disease that results primarily from pathogenic bacteria found within the mouth. It is a condition that arises due to poor oral hygiene but also as a result of certain disease states, in particular those associated with inflammatory states. Although treatment with antibiotics and oral intervention are usual treatments, even aggressive treatment of the bacterial infection fails to reduce gingival symptoms in some patients. Several lines of evidence suggest that alteration to Ca homeostasis, and disruption of SOCE in particular, in various cell types found in the mouth effect dental health.

Several reports in the literature reveal that various Ca channel blocker drugs influence dental health. For example, nifedipine and diltiazem, both Ca channel blocking agents used in the treatment of cardiovascular disease, have been linked to an increased risk of gingival enlargement (Miranda, J. et al. 2001. J. Periodontol. 72:605-611; Miranda, J. et al. 2005. J. Clin. Periodontol. 32:294-298). In an attempt to understand the mechanism underlying the association between gingivitis and Ca channel blocking drugs, it was found that the periodontal inflammatory infiltrate in patients treated with nifedipine had elevated numbers of lymphocytes, in particular B lymphocytes, and these cells decreased significantly in number following periodontal treatment (Bullon, P. et al. 2001. J. Clin. Periodontol. 28:897-903). Population-based observational studies have shown that the use of Ca channel blockers in the treatment of heart disease leads to an increased incidence of dental disorders in patients (Ellis, J. S. et al. 1999. J. Periodontal. 70:63-67; Miranda, J. et al. 2001. J. Periodontol. 72:605-611). These data concerning use of drugs that affect Ca homeostasis in cells are direct evidence for a role of Ca ion movement in the pathogenesis of gingivitis.

Specific evidence also suggests that SOCE in particular is involved in the pathogenesis of gingivitis, particularly in response to the presence of bacteria. SOCE has been implicated during infection of the spirochete *Treponema denticola*, a periodontal pathogen. Protein fractions including outer membrane from *T. denticola* inhibit inositol phosphate (Yang, P. F. et al. 1998. Infect. Immun. 66:696-702) and intracellular Ca flux in human gingival fibroblasts (Ko, K. et al. 1998. Infect. Immun. 66:703-709). Later research demonstrated that the major surface protein of *T. denticola* forms complexes on human gingival fibroblast plasma membranes, inhibiting SOCE and reducing ER Ca stores (Wang, Q et al. 2001. J. Biol. Chem. 276:23056-23064). Furthermore, dental disease with an inherited component, such as localized juvenile periodontitis (LJP), is a disease that is associated with an increased risk of gingivitis, as well as being linked to the presence of defective SOCE (Shibata, K. et al. 2000. J. Periodontol. 71:797-802). Therefore, data suggest that SOCE activity modulation is linked to pathogenesis of periodontal disease, specifically gingivitis.

It has now been found that the SOCE pathway is altered in a specific dose- and time-dependent manner in conditions modeling gingivitis. Further, a peptide derived from a mammalian gene has been found capable of restoring operation of SOCE, preventing the effects of gingivitis and other dental diseases.

In addition to an association of dental disease and gingivitis to SOCE activity, homeostasis of intracellular Ca is critical to cell survival. Many apoptotic stimuli are known to alter concentrations of Ca in the cytosol, storage of Ca in the ER, and/or uptake of Ca into the mitochondria (Pan, Z. et al. 2004. J. Biol. Chem. 279:19387-19390). In non-excitable cells, such as the prostate epithelia, elevation of cytosolic Ca usually results from release through Ca stores in the ER or entry from the extracellular Ca reservoir through activation of SOCE. Depletion of ER Ca stores serves as a signal to activate SOCE. Since Ca storage inside the ER is an essential indicator of a cell's proliferative, metabolic and apoptotic status, the retrograde signaling process from ER Ca depletion to SOCE activation is central to a broad range of cellular and physiological functions. As such, coordinated regulatory mechanisms must exist in the cell to ensure tight control of SOCE function. Aberrant function of SOCE could contribute to either the degenerative or tumorigenic nature of human diseases.

Therefore, in addition to applications in the prevention and treatment of dental diseases, any disease process where SOCE is integral to the pathogenic mechanisms could potentially be targeted by agents that modulate activity of SOCE, diseases related to apoptosis, such as cancer. It has now been found that SOCE activity is decreased in aged skeletal muscle and prostate cancer epithelial cells. The peptide of the present invention, which modulates activity of SOCE, would be useful for the treatment of diseases associated with apoptotic processes (e.g., aging, cancer). Moreover, the peptide of the present invention has application to a number of different human pathologies, across a wide variety of different tissues, as long as the pathology involves altered activity of SOCE.

SUMMARY OF THE INVENTION

An object of the present invention is a composition for increasing SOCE in a cell which comprises an isolated and purified P311 protein, or a mutant or variant form thereof, fused to a cell penetrating peptide and a pharmaceutically acceptable vehicle. In preferred embodiments the cells are mammalian gingival cells, skeletal muscle cells, or prostate cancer cells. The invention also envisions formulation of the composition as toothpaste, a dental rinse, or a food supplement.

Another object of the present invention is a method for increasing store-operated calcium entry in a cell which comprises contacting said cell with the composition which comprises an isolated and purified P311 protein, or a mutant or variant form thereof, fused to a cell penetrating peptide and a pharmaceutically acceptable vehicle, wherein contact of said cell with said composition results in an increase in the level of SOCE in the cell. In preferred embodiments, the cells are mammalian gingival cells, skeletal muscle cells, or prostate epithelial cells.

Yet another object of the present invention is a method for preventing or treating dental disease in an animal which comprises administering to said animal a therapeutically effective amount of the composition which comprises an isolated and purified P311 protein, or a mutant or variant form thereof, fused to a cell penetrating peptide and a pharmaceutically acceptable vehicle, wherein administration of said composition to said animal results in prevention or treatment of dental disease. In a preferred embodiment the dental disease is gingivitis. The method also envisions formulation of the composition as toothpaste, a dental rinse, or a food supplement.

Another object of the present invention is a method for treating muscle aging in an animal which comprises administering to said animal a therapeutically effective amount of the composition which comprises an isolated and purified P311 protein, or a mutant or variant form thereof, fused to a cell penetrating peptide and a pharmaceutically acceptable vehicle, wherein administration of said composition to said animal results in treatment of muscle aging.

Another object of the present invention is a method for treating cancer in an animal which comprises administering to said animal a therapeutically effective amount of the composition which comprises an isolated and purified P311 protein, or a mutant or variant form thereof, fused to a cell penetrating peptide and a pharmaceutically acceptable vehicle, wherein administration of said composition to said animal results in treatment of cancer.

DESCRIPTION OF THE DRAWINGS

FIG. 1 depicts the difficulty in mobilizing Ca stores in human embryonic palatal mesenchymal (HEPM) cells.

FIG. 3 depicts results of an experiment where the total Ca store in HEPM cells was depleted by acute or chronic application of lipopolysaccharide (LPS; 10 ng/mL for 3 or 18 hours).

FIG. 4 depicts results of an experiment where LPS's ability to uncouple SOCE in HEPM cells was demonstrated.

FIG. 5 depicts the results of experiments where the activity of the protein P311 is examined as a co-factor of SOCE in C2C12 myotubes.

FIG. 6 depicts results of experiments in Chinese Hamster Ovary (CHO) cells.

FIG. 10 depicts the results of experiments in Jurkat T cells.

FIG. 11 depicts results of experiments in Chinese Hamster Ovary (CHO) cells.

FIG. 13 depicts the results of experiments examining the level of P311 expression in muscle tissue (aged versus young).

FIG. 14 depicts results of experiments in NRP-Bax cells. SOCE was shown to be compromised in these cells.

DETAILED DESCRIPTION OF THE INVENTION

Figure 1A:
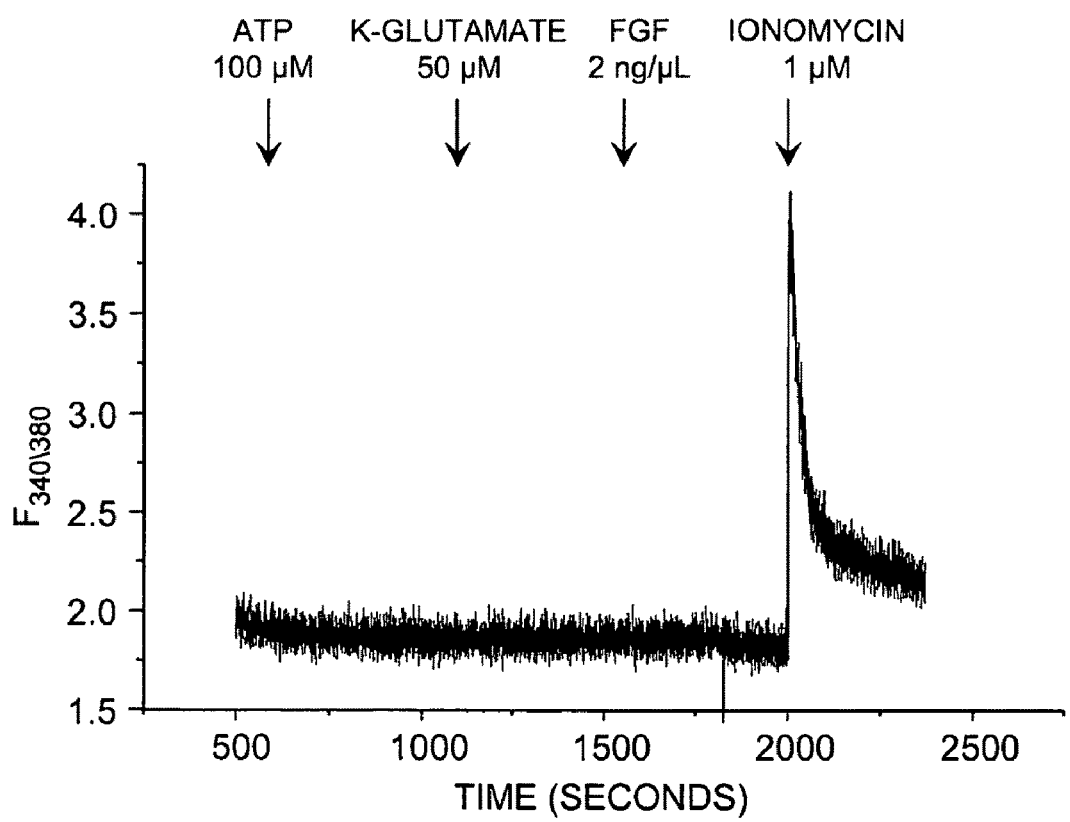
FIG. 1A shows the response over time when $10^6$ HEPM cells were loaded with Fura-2 and examined for Ca release in a PTI cuvette system. The cells were treated additively with adenosine triphosphate (ATP; 100 µM), κ-glutamate (50 mM), FGF (2 ng/µl) and ionomycin (1 µM).

The present invention includes compositions and methods for modulation of the activity of store-operated calcium entry (SOCE). Specific applications of the present invention include prevention and treatment of dental diseases, muscle aging, and cancer. A protein has been identified, P311. The P311 protein was shown to be capable of increasing the level of store-operated Ca entry in gingival cells and to prevent the effects of gingivitis and other dental diseases. Levels of the P311 protein have also been shown to be decreased in aged muscle tissue as compared to young muscle tissue, making strategies for increasing its levels in aging muscle another part of the present invention. It has also been shown that reduced levels of SOCE are present in prostate cancer cells, making strategies for increasing levels of SOCE through administration of P311 a method for inducing apoptosis and treating cancer. Therefore, the present invention includes compositions and methods for prevention and treatment of dental diseases, muscle aging and cancer in animals, including humans.

In the context of the present invention, "modulation" of SOCE is defined as increasing or decreasing the level of SOCE in a cell or tissue. Also in the context of the present invention, dental diseases that can be treated would include any dental disease whose pathogenesis if related to al altered level of SOCE. In the context of the present invention "prevention" of a disease is defined as a reduction in the likelihood or risk of developing a disease. In the case of a disease such as gingivitis, this can be assessed objectively by determining whether there is an active inflammatory process present in tissues of the mouth and then determining whether administration of the compositions of the present invention reduce the level of inflammation. In the context of the present invention "treatment" of a disease is defined as a reduction in the symptoms of the disease. In the case of gingivitis, the symptoms reduced would include but not be limited to bleeding of the gums or redness of the gums. In the case of muscle aging, the symptoms reduced would include but not be limited to muscle atrophy, muscle wasting, and decreased muscle strength. In the case of cancer, the symptoms reduced would include but not be limited to tumor size, tumor metastases, or rate of tumor cell growth. Also in the context of the present invention, a "therapeutically effective amount" or an "effective amount" is defined as the amount of the composition that needs to be administered in order to result in a reduction in the likelihood of a disease or a reduction in the symptoms of a disease.

Experiments were initially carried out to determine whether perturbation of Ca homeostasis through modulation of store-operated calcium entry (SOCE) and/or Ca release from the endoplasmic reticulum (ER) in cells associated with dental structures (e.g., gingival cells) induce cellular dysfunction that leads to progression of gingivitis. The model system used for these experiments was Ca handling in a cell culture system of human embryonic palatal mesenchymal (HEPM) cells. The cell system had been identified by others as an appropriate model for examining the function of cells of the human gum (Yoneda, T. and R. M. Pratt. 1981. *Science* 213: 563-565), and has even been used as a model to correlate with in vivo results (Jannesson, L. et al. 2004. *J. Clin. Peridontol.* 31:91-94). Therefore, results from the in vitro cell culture studies would be understood by one of skill to be predictive of results in vivo in humans.

Figure 1B:
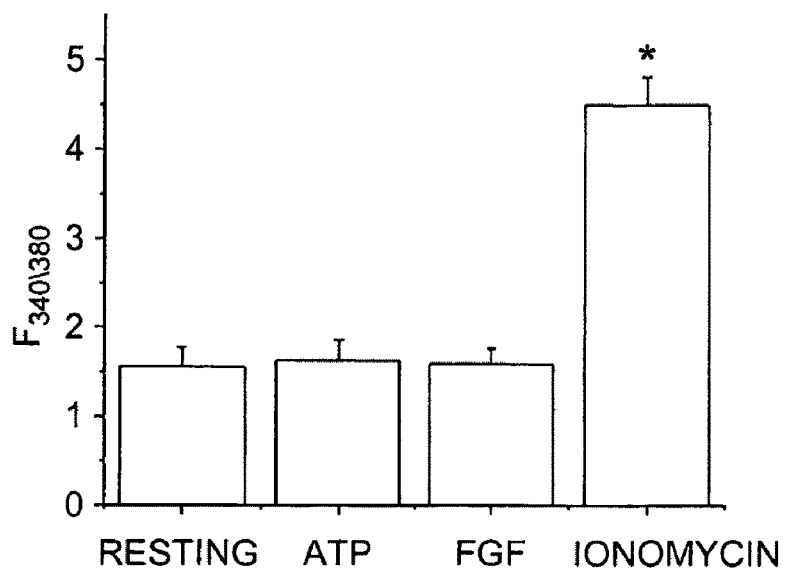
FIG. 1B depicts the responses in summary form as the mean±SE (*p<0.05).

Studies of the Ca handling characteristics in HEPM cells revealed the cells possess a large tightly controlled intracellular Ca store and a robust extracellular Ca entry mechanism through SOCE. HEPM cells were not responsive to classical methods of mobilizing Ca from endoplasmic reticulum (ER) stores, such as application of ATP and potassium (see FIG. 1). However, disruption of membranes allowing non-specific Ca flux by ionomycin reveals a large store of Ca available for release within the cell. These findings indicated that while large quantities of Ca are stored within HEPM cells, there are adaptive mechanisms present to prevent the aberrant release of this Ca, which would be detrimental to cell function and survival.

Figure 2:
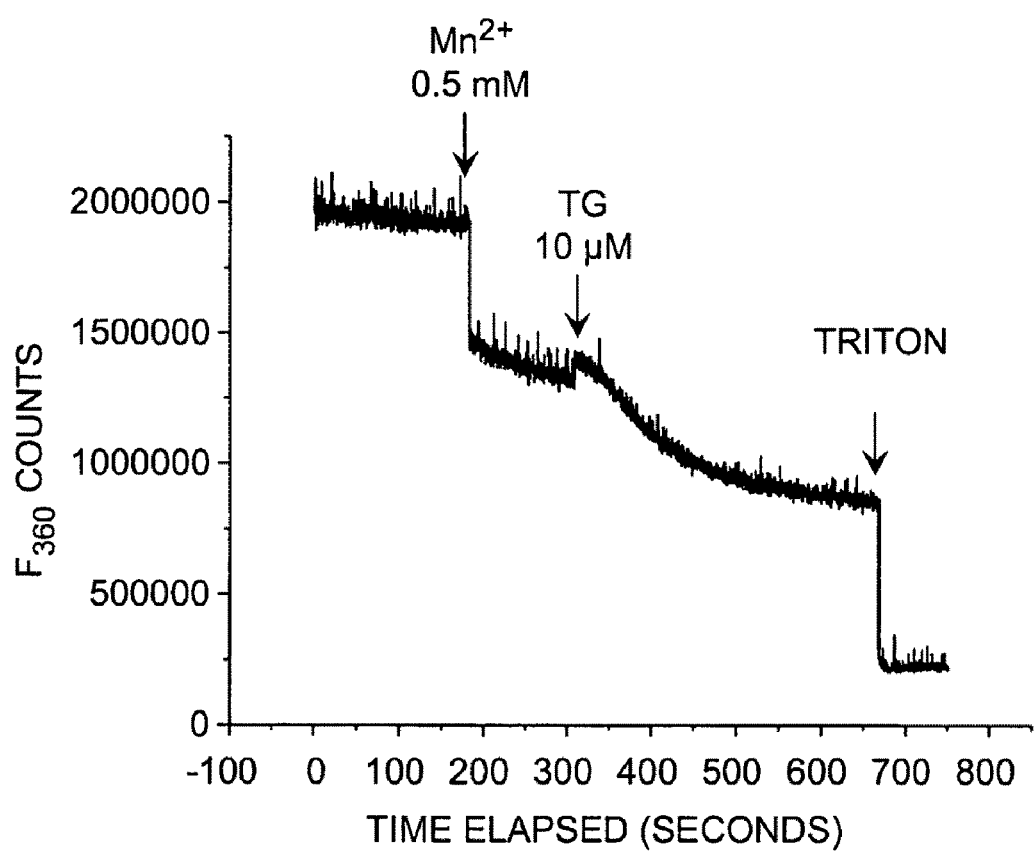
FIG. 2 is a representative tracing of the Fura-2 quenching resulting from manganese (Mn) entry through SOCE machinery. Thapsigargin (TG; 10 µM)) was used to induce Ca store depletion and Triton was used to confirm cellular integrity and indicate the basal fluorescent signal.
Figure 4A:
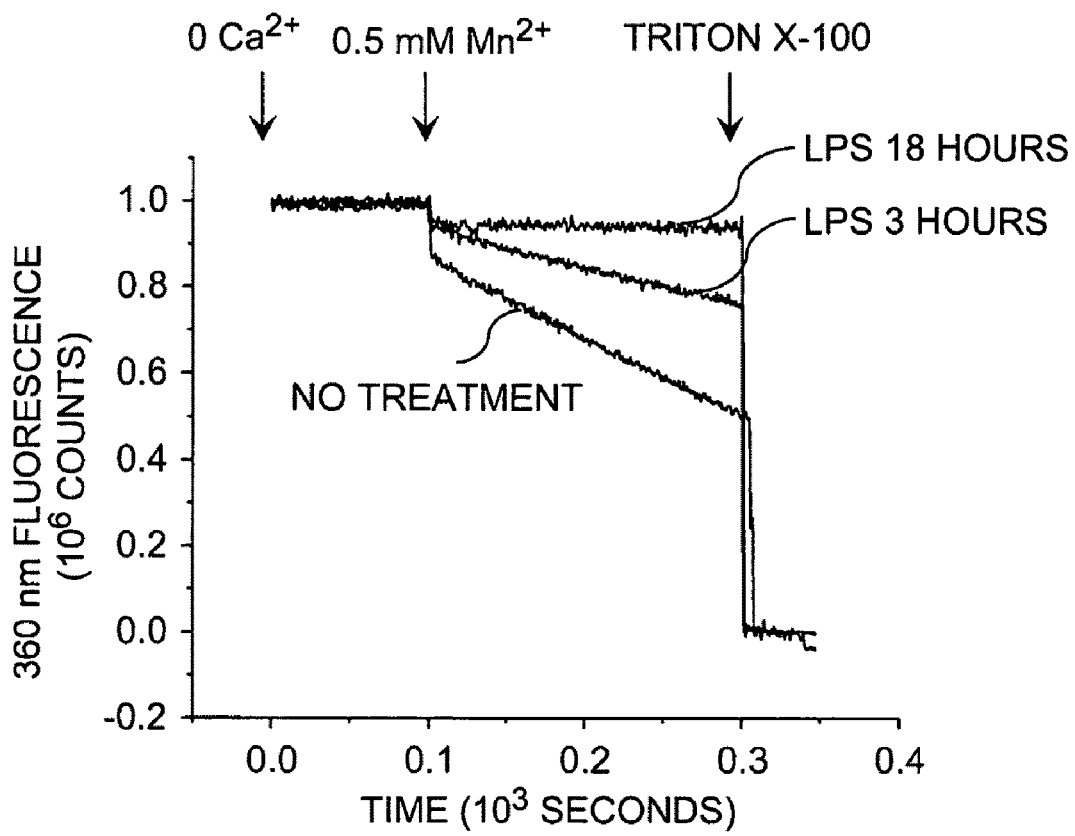
FIG. 4A depicts results when $10^6$ HEPM cells were loaded with Fura-2 and the rate of Mn quenching was determined following treatment with ionomycin (1 µM). Addition of ionomycin to the culture resulted in differing responses depending on the treatment (no treatment; LPS for 3 hours; LPS for 18 hours).
Figure 4B:
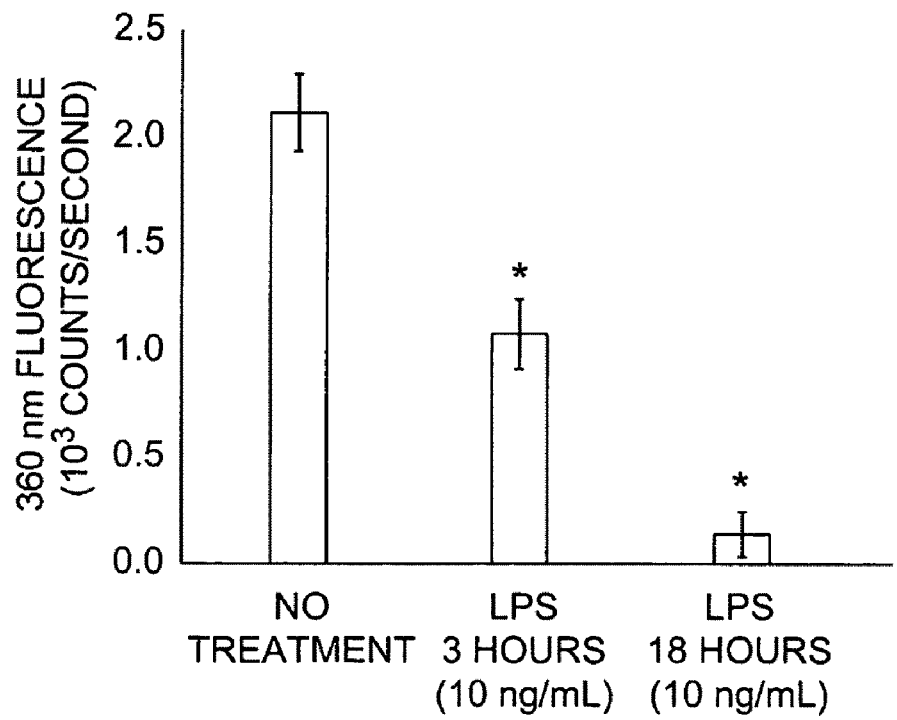
FIG. 4B depicts the responses in summary form as mean±SE (*p<0.05).

Additional studies revealed that depletion of ER Ca stores resulted in rapid activation of SOCE in HEPM cells. This induction was seen following Ca store depletion induced by the application of thapsigargin (TG), an inhibitor of the sarco/endoplasmic reticulum ATPase Ca pump (SERCA), (see FIG. 2) or ionomycin (see FIG. 4). These experiments indicated that robust SOCE is present in HEPM cells, making these cells an ideal model system to examine the influence of the Ca signaling state on the health of cells during gingivitis.

Figure 3A:
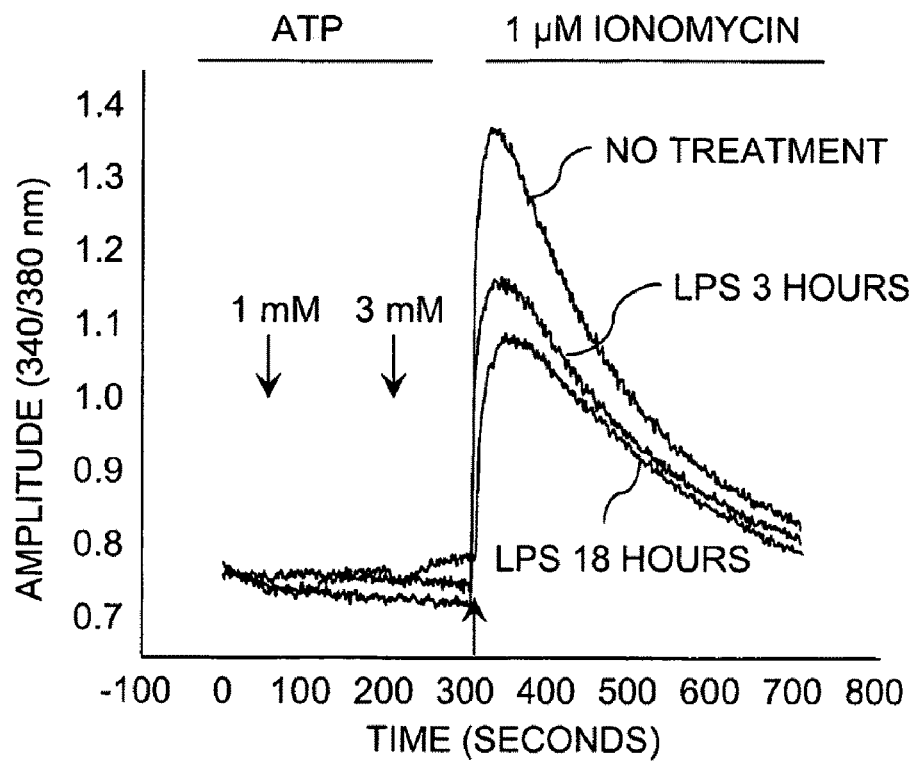
FIG. 3A depicts the results when $10^6$ HEPM cells were loaded with Fura-2 and examined for Ca release in a PTI cuvette system. ATP stimulation (1 or 3 mM) had no effect on LPS-treated cells. Addition of ionomycin (1 µM) to the culture resulted in differing responses depending on the treatment (no treatment; LPS for 3 hours; or LPS for 18 hours).
Figure 3B:
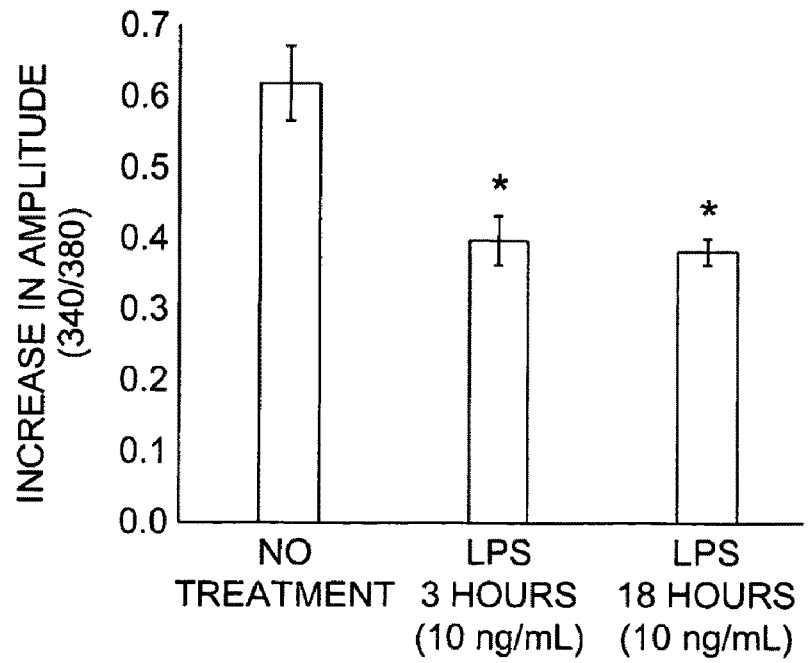
FIG. 3B depicts the responses in summary form as mean±SE (*p<0.05).

A major mediator of the gingival inflammatory response induced by bacteria is lipopolysaccharides (LPS). Therefore, experiments were performed where a disease state was induced in HEPM cells through acute (3 hours) and chronic (18 hours) LPS application. Changes in total Ca store and SOCE were measured after the LPS treatments. The results showed that application of LPS resulted in reduction of the HEPM Ca store with both acute (3 hours) and chronic (18 hours) of exposure to LPS (see FIG. 3). The effects of LPS on Ca stores appear to be rapidly induced, as the 3 hour treatment was as effective as 18 hour treatment in modulating Ca activity. The decrease in Ca stores following LPS application indicated that SOCE was disrupted by LPS, since SOCE is the primary mechanism many cells use to replenish their intracellular Ca stores from the available reservoir of extracellular Ca.

To establish that SOCE in HEPM cells was disrupted by application of LPS, experiments were performed where the rate of manganese (Mn) quenching of Fura-2 fluorescence at both acute and chronic time points was examined. Despite the presence of a reduced Ca store under these conditions (see FIG. 3), LPS treatment resulted in a drastic uncoupling of ionomycin-induced SOCE (see FIG. 4). The effect of LPS on SOCE seemed to be time dependent, with near complete repression of SOCE by 16 hours. After 3 hours, the uncoupling of SOCE was not as pronounced, however the repression was still sufficient to significantly diminish the Ca store in treated HEPM cells (see FIG. 3). Additional experiments demonstrated that LPS treatment produced similar levels of inhibition of SOCE activity induced by TG.

These results demonstrated that SOCE activity is uncoupled by treatment of HEPM cells with LPS, and that such uncoupling is a mechanism underlying the pathogenesis of gingivitis in mammalian organisms, including humans. The uncoupling of SOCE would lead to chronic Ca store depletion, which has been shown to result in disrupted cellular function and cell death.

Restoration of SOCE towards basal levels should alleviate the effects of bacterial LPS on the cells of the mouth, and modulate the severity of gingivitis. Therefore, experiments were performed to examine the effect of restoring SOCE on HEPM cells. Any drug or agent that is capable of regulating or modulating SOCE in cells such as gingival cells would be a candidate for testing. Experiments were performed to identify proteins capable of regulating SOCE activity in mammalian cells.

The C2C12 myogenic cell line was used as a model system because the expression of SOCE is developmentally regulated in these cells. SOCE is absent in the myoblast stage, and is induced upon differentiation and myotube formation. It was thought the elevation of SOCE associated with myotube formation in these cells was related to one of two events: 1) the expression of the pore-conducting unit of SOC leading to an increase in muscle differentiation; or 2) the expression of cytosolic factors that participate in retrograde signaling from SR Ca depletion to SOCE activation that is activated during muscle differentiation. Experiments were performed using the DNA MicroArray method to search for possible changes in gene expression associated with the up-regulation of SOCE in C2C12 myotubes. mRNAs isolated from C2C12 cells at the myoblast and myotube stages were analyzed by subtraction, allowing identification of ~800 genes that were significantly unregulated (>3 fold) in the myotube stage. Considering these 800 genes, the majority displayed signatures of muscle differentiation (e.g. myosin, RyR, dihydropyridine receptor, caveolin-3 etc.). Only 87 of the genes were novel with undefined physiological functions. With this limited number of candidate genes, a shRNA approach to knockdown expression of these target genes was employed in an effort to identify putative genes that were associated with the function of SOCE. From an initial screen of 12 genes, one cytosolic target gene was identified which was named P311. This protein contained 68 amino acids (with an estimated molecular weight of 8 kDa). Using BLAST search tools, P311 was identified as p311 (SEQ ID NO: 1), a ubiquitous protein that exists in both excitable and non-excitable cells, including the prostate epithelia. P311 was initially isolated from a group of proteins screened after their release was induced in cells due to the activity of pentylenetetrazol (PTZ; Kajiwara, K. et al. 1995. *Brain Res.* 671:170-174). PTZ is a drug used for clinical treatment of neurological depression. The p311 protein is an 8 kDa polypeptide that is rapidly (minutes) degraded in test systems (Taylor, G. A. et al. 2000. *J. Biol. Vhem.* 275:4215-4219).

Figures 7, 8:
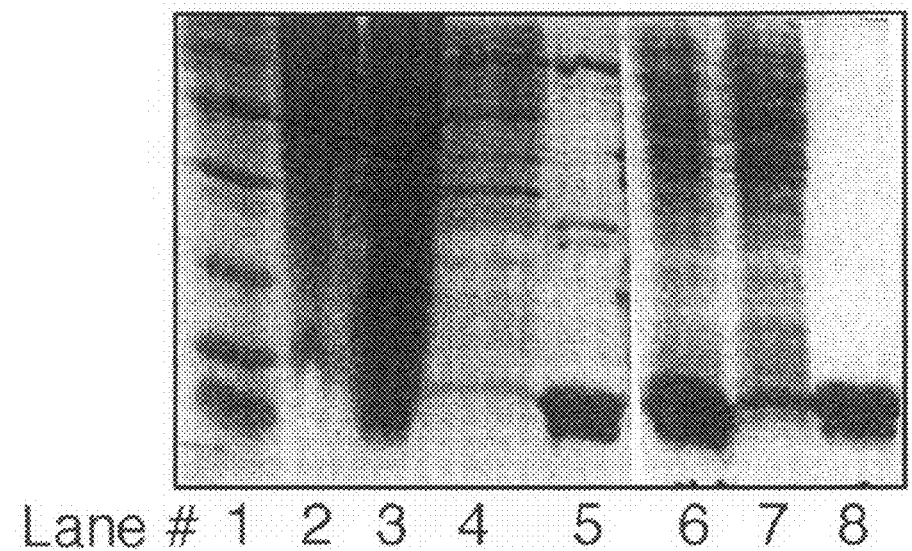
FIG. 7 depicts results of experiments directed to purification of P311. Lane 1, MW markers; lanes 2, 3 & 6, crude cell extract; lanes 4 & 7, supernatant; lane 5, eluent from Ni-resin; lane 8, P311 after gel filtration.
FIG. 8 depicts the sequence homology between the P311 mouse protein sequence (SEQ ID NO: 10), the P311 human protein sequence (SEQ ID NO: 1) and the cyclophilin-like peptide (SEQ ID NO: 11).

Experiments were performed to examine the structure of the P311 protein. Examination of the full sequence of P311 revealed the existence of prolyl isomerase structural domains. The primary amino acid sequence alignment of P311 protein is shown in FIG. 8, and that analysis predicted that the P311 protein may contain intrinsic enzymatic activity to facilitate prolyl isomerase activity. Conformational changes mediated by prolyl isomerase in ion channels have been shown to regulate ion channel opening properties, such as the cystic fibrosis transmembrane conductance regulator openings (CFTR; Xie, J. et al. 2000. *Biophys. J.* 78:1293-1305). Interestingly, putative cytosolic segments of Orai1 (Prakriya, M. et al. 2006. *Nature* 443:230-233; Vig, M. et al. 2006. *Curr. Biol.* 16:2073-2079) and STIM1 (Liou, J. et al. 2005. *Curr. Biol.* 15:1235-1241; Roos, J. et al. 2005. *J. Cell. Biol.* 169:435-445), both known to be mediators of SOCE (Peinelt, C. et al. 2006. Nat. Cell. Biol.), contain multiple proline residues, with some residues located within conserved sequences or functional motifs. However, the role of the proline-rich motifs in STIM1 and Orai1 on SOCE function has not been examined.

Figure 5A:
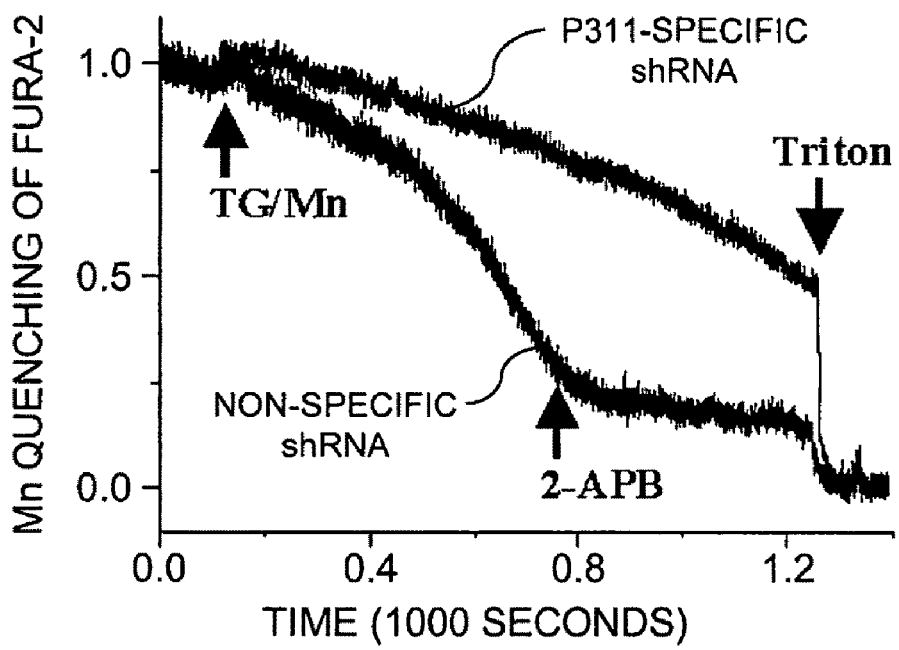
FIG. 5A depicts the results when myotubes were transfected with non-specific shRNA (as a control), and the function of SOCE was completely ablated; TG depleted sarcoplasmic reticulum (SR) Ca and initiated Mn entry through SOCE, which can be blocked by 2-APB (20 µM). SOCE is suppressed in myotubes transfected with specific shRNA against P311. Permeablization of cells by Triton X-100 (0.5%) allowed complete quenching of Fura-2 by Mn.
Figure 5B:
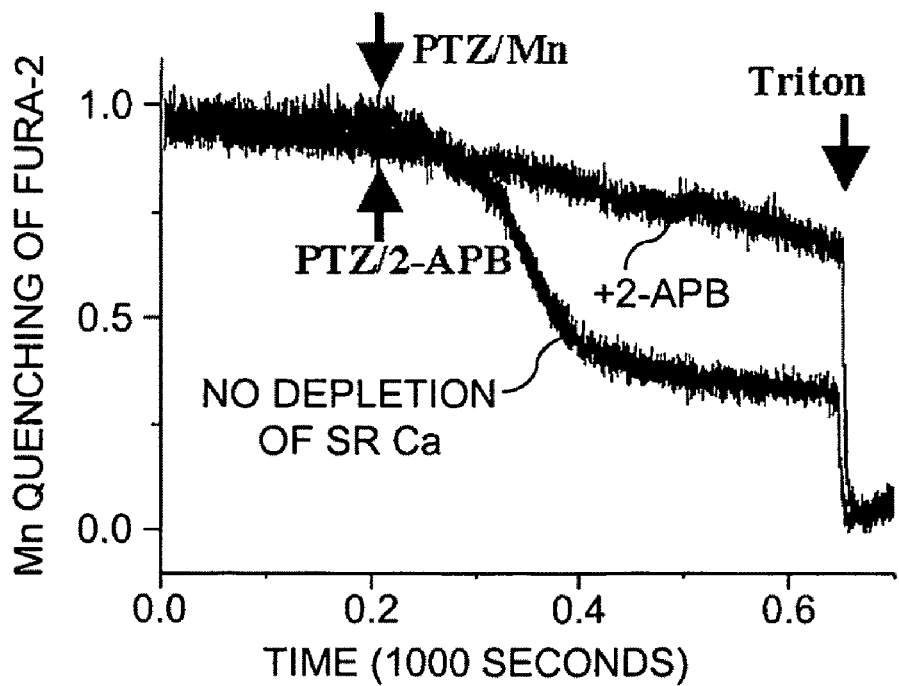
FIG. 5B depicts results of experiments where addition of 20 mM PTZ initiates Mn entry into C2C12 myotubes without depletion of SR Ca, and this effect can be blocked by 2-APB.
Figure 5C:
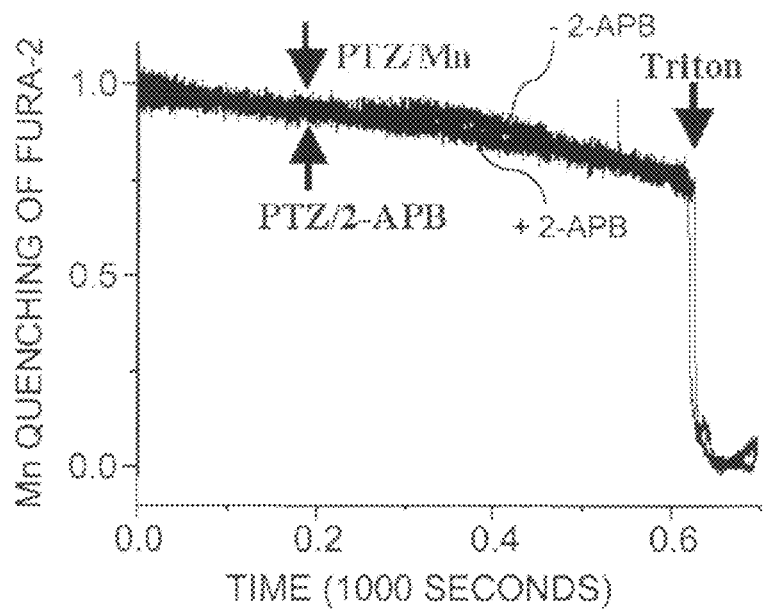
FIG. 5C depicts results of experiments where in C2C12 myotubes transfected with shRNA against P311, PTZ has no effect of SOCE in the absence or presence of 2-APB. shRNA sequence was cloned into the pCMS-EGFP, which provides convenient selection of transfected cells.

With the identification of a putative SOCE regulating agent, P311, experiments were performed to demonstrate that P311 was capable of regulating SOCE activity. Transfection of shRNA against P311 into C2C12 myotubes resulted in complete ablation of the function of SOCE (see FIG. 5A). In addition, treatment of C2C12 myotubes with PTZ induced the activation of SOCE, without affecting the SR Ca filling status (see FIG. 5B). PTZ-triggered Mn quenching of Fura-2 fluorescence was inhibited by 2-aminoethoxydiphenyl borate (2-APB), a known blocker of SOCE (Peppiatt, C. M. et al. 2003. *Cell. Calcium* 34:97-108). The effect of PTZ was absent in shRNA-treated myotubes, confirming that P311 is the cytosolic target for PTZ (see FIG. 5C).

Additional experiments were performed where a GFP-P311 fusion protein was generated and the ability of this fusion protein to modulate SOCE was tested in another cell line, Chinese Hamster Ovary (CHO) cells. The results showed that the GFP-P311 fusion protein induced SOCE in CHO cells, indicating that P311 regulates regulate SOCE activity in multiple cell types (see FIG. 6C).

Figure 6A:
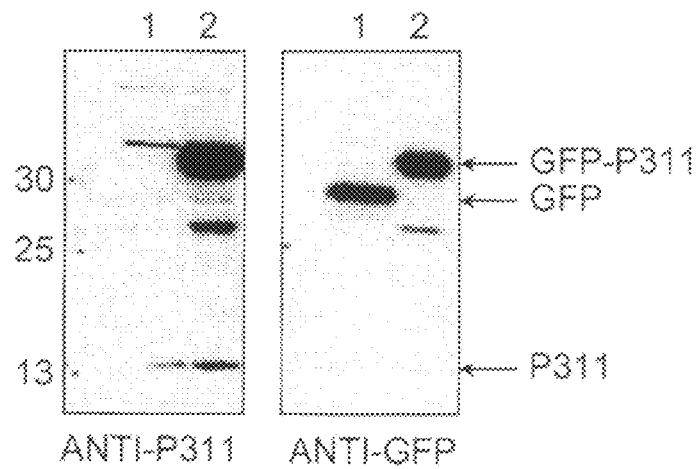
As shown in FIG. 6A, the anti-P311 antibody recognized endogenous P311 present in CHO cells as well as the GFP-P311 fusion protein transiently expressed in CHO cells. Lane 1—CHO cells transfected with GFP; lane 2—CHO cells transfected with GFP-P311. Left panel was blotted with anti-P311, and right panel was blotted with anti-GFP.
Figure 6B:
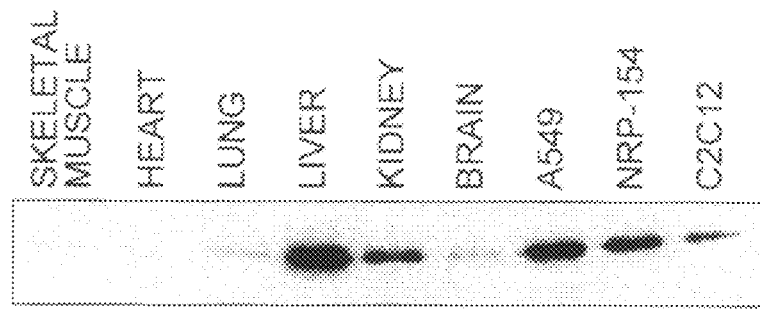
FIG. 6B depicts results of Western blot analyses. The results demonstrated that P311 was ubiquitously present in all mouse tissues, as well as in cells of A549, a human lung cancer epithelial cell line, cells of NRP-154, a rat prostate epithelial cancer cell line, and cells of C2C12, a mouse skeletal muscle myogenic cell line.
Figure 6C:
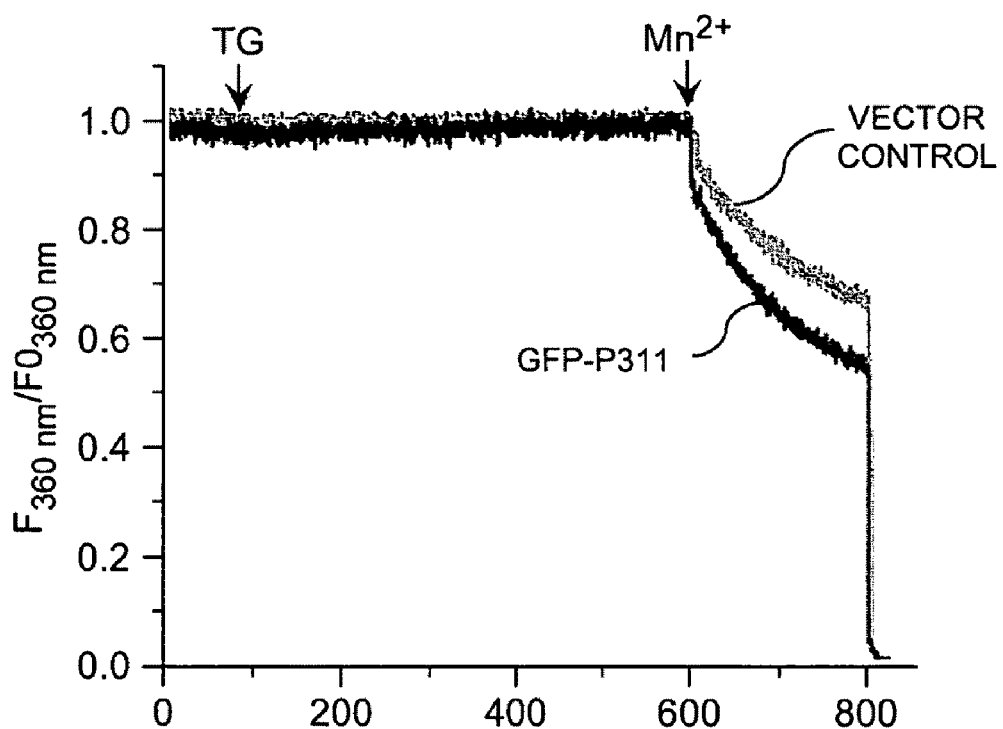
FIG. 6C and FIG. 6D show that the overexpression of GFP-P311 increasing SOCE in CHO cells.
Figure 6D:
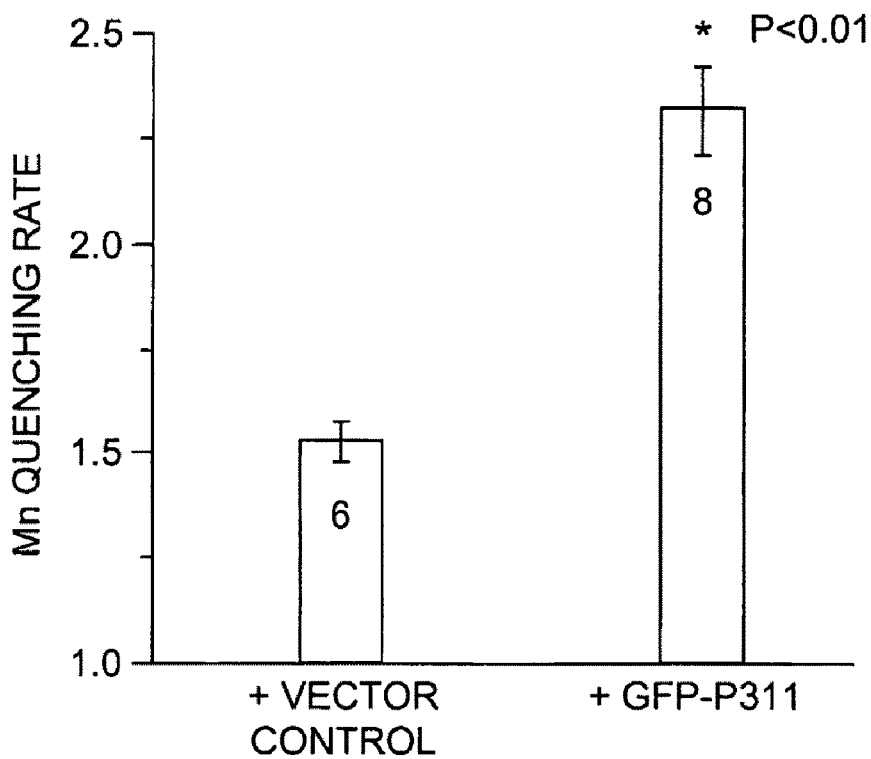

The expression pattern of P311 was determined in mice using a P311-specific antibody (see FIG. 6B). The results showed that P311 is ubiquitously expressed, as would be expected from a general regulator of the SOCE pathway found in numerous different cell types.

Therefore, P311 is a protein that can be used in animals, including humans, to modulate activity of SOCE. In the present invention, P311 is a composition for prevention and treatment of dental disease. P311 acts to prevent and treat dental disease by increasing the level of SOCE in tissues and cells where disease processes have inhibited or reduced the level of SOCE.

With experiments having established the utility of modulating SOCE activity in treating dental disease, other applications for the composition of the present invention, the P311 peptide, were sought. Experiments were performed examining the role of SOCE in muscle aging and in the pathogenesis of cancer. Other experiments were performed to examine in more detail the interaction of P311 with SOCE molecular machinery.

Figure 9A:
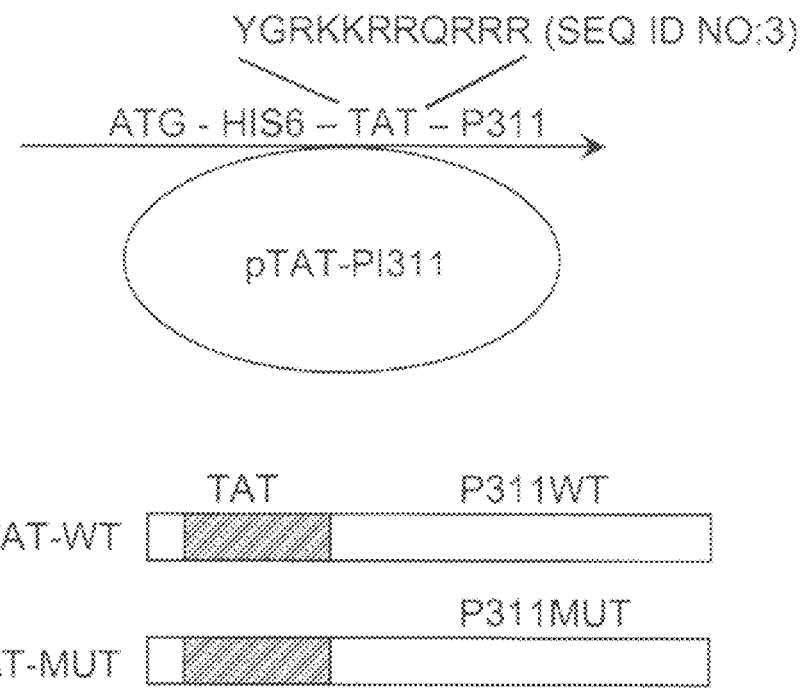
FIG. 9 depicts the purification of TAT-P311. TAT-311 eluted with >95% homogeneity.
Figure 9B:
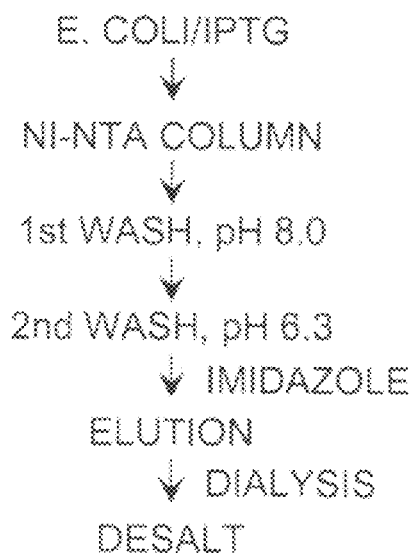
Figure 9C:
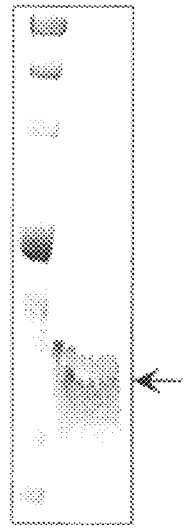

The first additional experiments performed were aimed at optimizing the production of recombinant P311 fused with a cell-penetrating peptide. The cell-penetrating peptide used was TAT. Extensive studies have shown that an 11-amino acid TAT peptide "YGRKKRRQRRR" (SEQ ID NO: 2) can mobilize peptides of various sizes to penetrate the cellular membrane (Morris, M. C. et al. 2001. *Nat. Biotechnol.* 19:1173-1176). For example, intraperitoneal injection of a 120-kD β-galactosidase protein, fused to the TAT sequence, resulted in delivery of the biologically active fusion protein to all tissues in mice (Cal, S. R. et al. 2006. *Eur. J. Pharm. Sci.* 27:311-319). This method has also been used to deliver a presenilin loop peptide into cells (Cai, C. et al. 2006. *J. Biol. Chem.* 281:16649-16655). The cDNA encoding P311 was subcloned behind the His-TAT sequence, for purification of the TAT-P311 fusion protein from *E. coli*, using a Ni-affinity column (see FIG. 9). Using this method, the production of the P311-TAT peptide was optimized over previously reported methods.

Figure 10A:
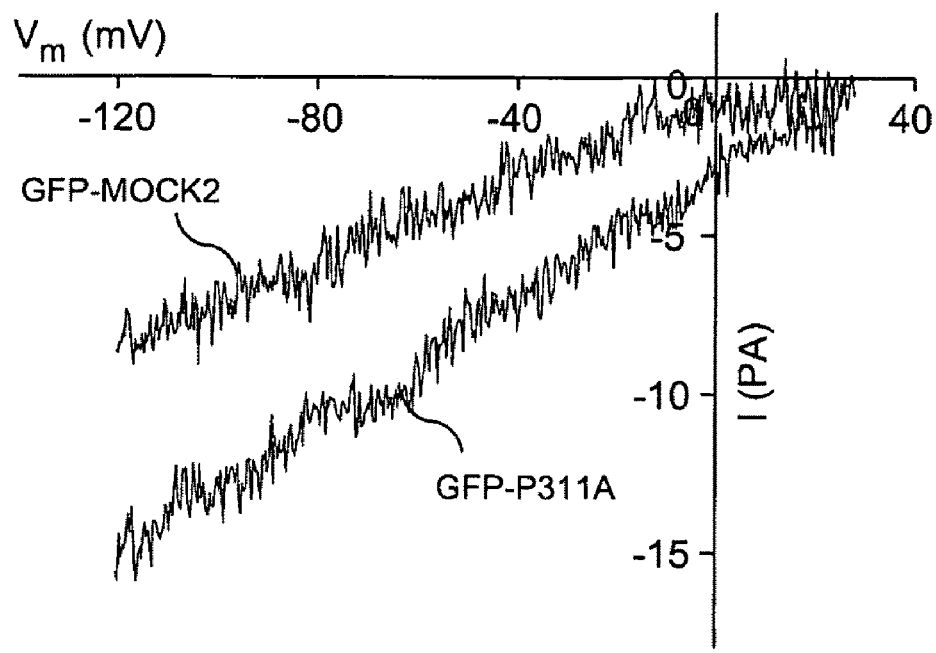
FIG. 10A show that expression of GFP-311 enhances $I_{CRAC}$ in Jurkat cells.
Figure 10B:
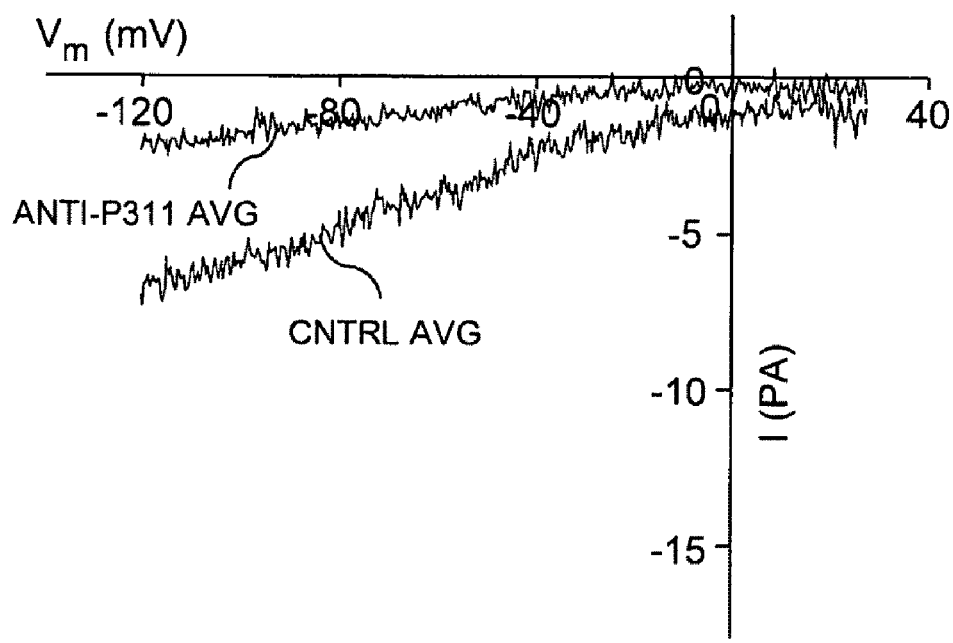
FIG. 10B depicts results when endogenous P311 activity was knocked down in Jurkat cells using shRNA against P311, which diminishes $I_{CRAC}$.

Next, the relationship of P311 activity in immune cells and SOCE function was examined. The Ca-release activated current ($I_{CRAC}$) in Jurkat T-lymphocytes has been traditionally used to study the electrophysiological characters of SOCE in non-excitable cells (Lewis, R. S. and M. D. Cahalan. 1989. *Cell. Regul.* 1:99-112; Premack, B. A. et al. 1994. *J. Immunol.* 152:5226-5240). To test whether the effect of P311 on SOCE in excitable cells, such as skeletal muscle, is also applicable to non-excitable cells, GFP-P311 was over-expressed, or P311 was silenced with a specific shRNA probe against the human P311 sequence in Jurkat cells. To monitor the shRNA-targeted cells, RFP was used as a reporter gene (transcription driven by a separate promoter). The standard whole-cell configuration was used to measure the $I_{CRAC}$ current. A ramp test pulse protocol (100 ms duration, ranging from −130 mV to +30 mV) was applied every 2 s. Upon establishment of the whole-cell configuration, cells were perfused with Ca-free solution containing 2 µM thapsigargin, allowing passive depletion of the ER Ca store and activation of $I_{CRAC}$. After ~3 minutes, extracellular Ca was raised to 20 mM in order to monitor Ca flux through CRAC channels. Averaged leak current observed in the Ca-free condition was subtracted from the test current obtained in the presence of 20 mM external Ca in order to isolate $I_{CRAC}$. Results of the studies are shown in FIGS. 10A and 10B. These data demonstrated that over-expression of GFP-P311 could enhance $I_{CRAC}$ in Jurkat cells compared with cells transfected with GFP vector. Moreover, transfection of shRNA against P311 significantly decreased $I_{CRAC}$ in cells as compared to cells transfected with scrambled shRNA sequence. These data demonstrated that $I_{CRAC}$, and correspondingly SOCE, was directly regulated by P311 in Jurkat cells.

Figure 11A:
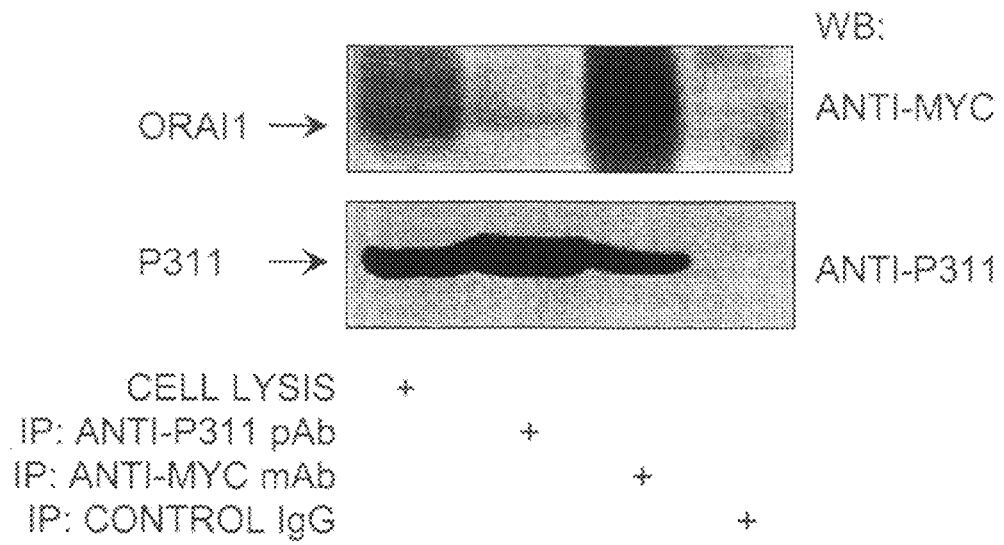
In FIG. 11A, CHO cells were co-transfected with GFP-myc-Orai1 and STIM1. Western blot shows that anti-myc antibody could pull-down P311, while anti-P311 pAb but not normal rabbit IgG precipitated GFP-myc- Orai1.
Figure 11B:
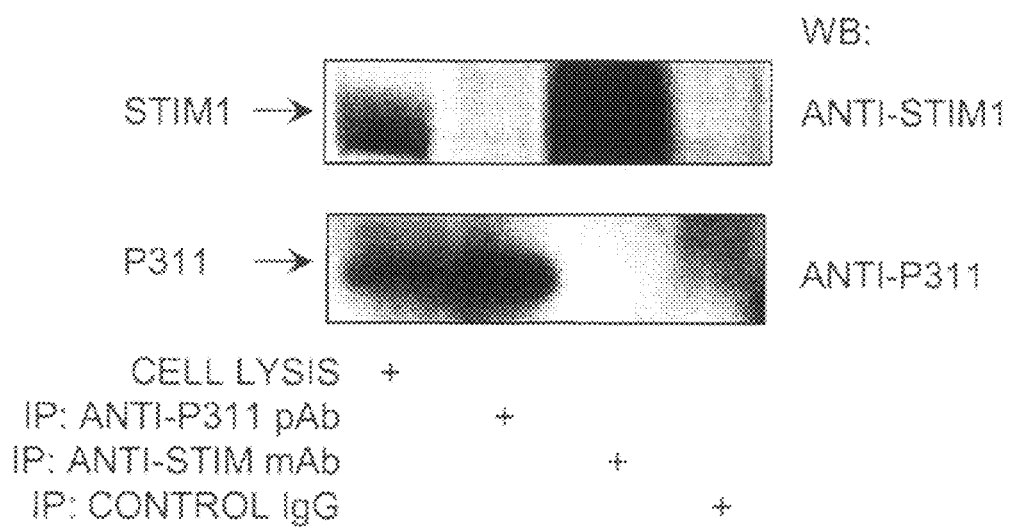
In FIG. 11B, anti-P311 pAb could not pull down STIM1, while anti-STIM1 mAb also failed to immunoprecipitate P311.

Next, the interaction of P311 with SOCE molecular machinery was examined experimentally. The interaction of P311 with known components of SOCE, such as STIM1 and Orai1, was studied. A GFP-myc-Orai1 plasmid and the mammalian expression plasmid containing the human STIM1 cDNA (OriGene, Inc.) were used. The plasmids were transfected into CHO cells and 36 hours after transfection, total cell lysates from CHO cells transiently expressing GFP-myc-Orai1 were incubated with either a polyclonal antibody against P311, or an anti-myc monoclonal antibody, with normal rabbit IgG serving as the control. Results of a co-immunoprecipitation (co-IP) assay revealed a physical interaction between P311 and Orai1, since immunoprecipitation with anti-myc pulled down P311 and immunoprecipitation with anti-P311 pulled down GFP-myc-Orai1 (see FIG. 11A). Using similar approaches, it was found that STIM1 could not immunoprecipitation with anti-P311 and P311 could not immunoprecipitation with anti-STIM1 antibody (see FIG. 11B). Similar results were obtained when co-IP assays were repeated using reversible cross-linker DSP and different detergents in cell lysis buffer, including Triton X-100, NP-40 and CHAPS. Although negative results from co-IP between P311 and STIM1 cannot rule out the potential in vivo interaction between the two proteins, the positive results from the co-PI assays between P311 and Orai1 indicated that the primary target of P311 in the multi-molecular SOCE complex is Orai1.

Figure 12:
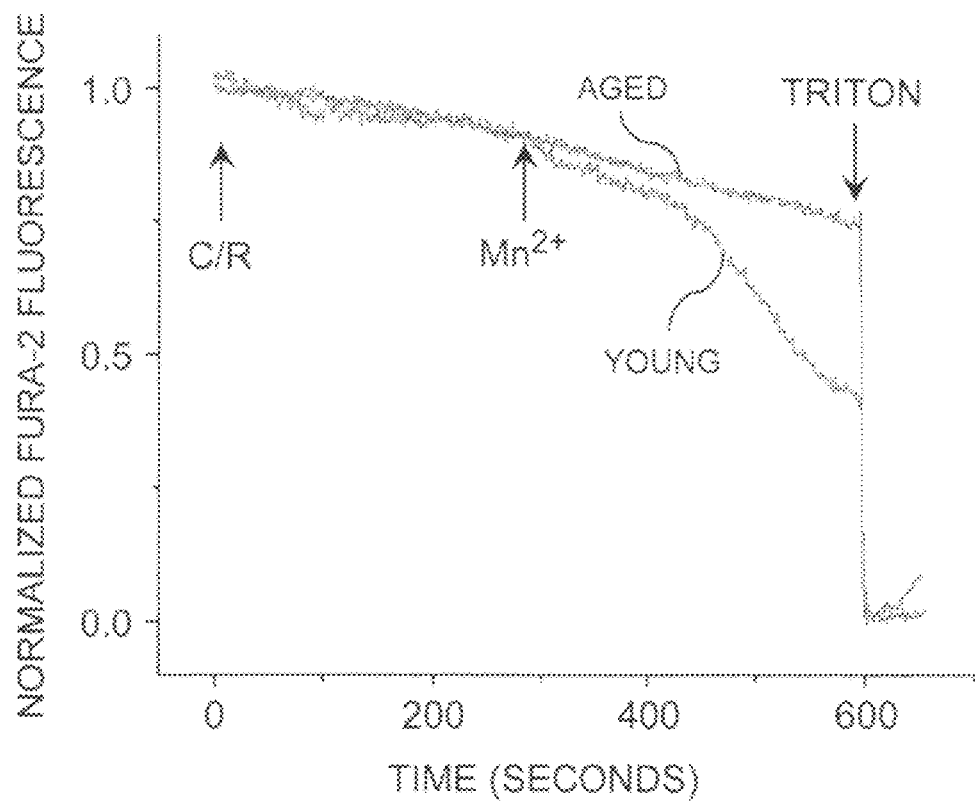
FIG. 12 depicts results of experiments in aged muscle cells examining activity levels of SOCE. Normalized $Mn^{2+}$ quenching of Fura-2 at excitation wavelength 360 nm illustrated activation of SOCE in flexor digitorum brevis (FDB) muscle fibers following caffeine/ryanodine (C/R)-induced depletion of SR Ca store in young and aged muscle fibers.

With this additional information on the interaction of P311 with SOCE molecular machinery, further experiments were then performed to examine the activity of SOCE in tissues, as well as the potential therapeutic applications for P311. The tissue chosen for study was aging skeletal muscle. It had been shown that the effects of aging on skeletal muscle function are associated with denervation of muscle fibers, remodeling, and loss of motor units (Larsson, L. 1995. *J. Gerontol. A. Biol. Sci. Med. Sci.* 50:91-95). Because functional alterations occur before significant muscle wasting becomes evident, changes in the excitation-contraction coupling machinery and intracellular Ca homeostasis may act as causative factors for, or adaptive responses to, muscle aging (Delbono, O. 2002. *Biogerontology* 3:265-270; Faulkner, J. A. et al. 1995. *J. Gerontol. A. Biol. Sci. Med. Sci.* 50:124-129). To study the role of SOCE in muscle aging, the status of SOCE activation in young and aged skeletal muscle was examined. The results showed that thapsigargin- or caffeine-induced activation of SOCE in aged skeletal muscle is severely compromised (see FIG. 12).

Figure 13A:
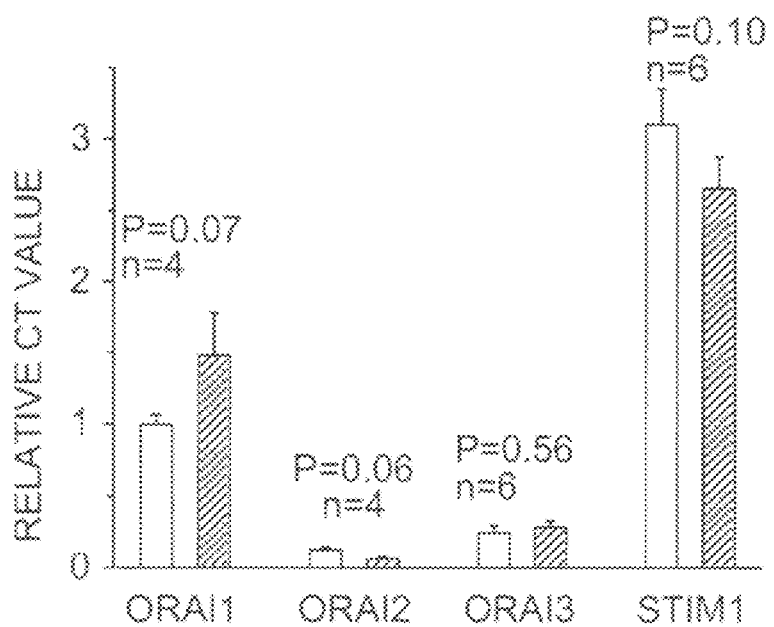
FIG. 13A shows real time PCR data from aged and young muscle samples with primers specific to Stim1 or Orai. There was no statistically significant difference between mRNA levels. Data shown here are normalized to the Ct value of GAPDH and the average Ct of Orai1 was set as 1.

Experiments were then performed to investigate the cause for reduced SOCE in aged muscles. Several genes involved in SOCE activation were examined using real-time PCR. In adult mouse skeletal muscle, it was found that the dominant Orai isoform expressed was Orai1, indicating that Orai1 comprised the principal pore-forming unit for SOCE in skeletal muscle (see FIG. 13A); mRNA for Orai2 and Orai3 were detected at lower levels. No significant changes in mRNA for STIM1 or Orais were identified in aged mouse skeletal muscle. Western blot further confirmed that STIM1 expression levels remained unchanged in young and aged skeletal muscles. Thus, an age-related decrease in SOCE activity is not likely due to changes in the relative abundance of STIM1/Orai1, but instead other factors may be involved in the reduced activity of SOCE associated with muscle aging.

Figure 13B:
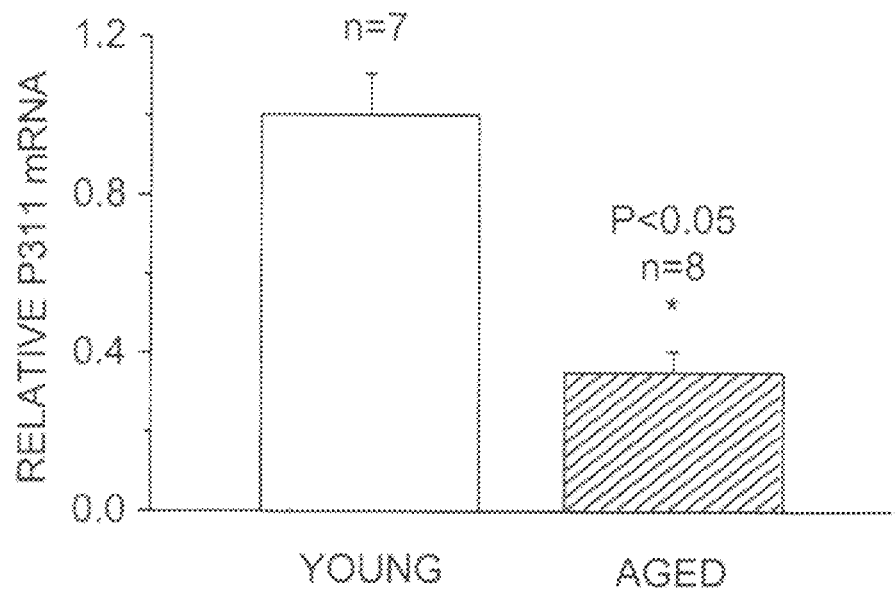
FIG. 13B shows real time PCR data with primers specific to P311 from aged and young muscle samples.
Figure 13C:
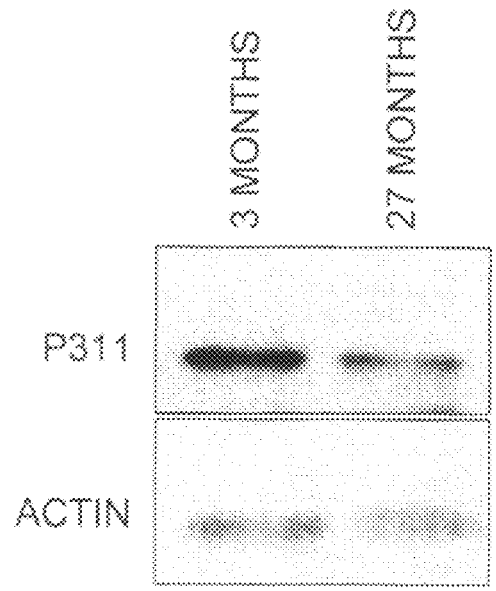
FIG. 13C shows Western blots of P311 in skeletal muscles. Young mice were 3 months while aged or "old" mice were 27 months.

As shown in FIG. 13, mRNA of P311 exhibits about a 2-fold decrease in aged muscle as compared with young muscle. Western blot results further confirmed that the P311 protein level was decreased in aged skeletal muscle (see FIG. 13). Therefore, restoration of P311 expression in aged skeletal muscle is a desirable method for improving SOCE activity and allowing for improved skeletal muscle performance in aged patients.

The additional application for P311 studied was the relationship of SOCE activity to the pathogenesis of cancer, and the potential utility of P311 in cancer treatment. In early stage prostate cancer, the prostate tumor parenchyma is androgen-dependent. Androgen ablation, an employed therapeutic strategy, causes profound apoptosis of tumor epithelium. However, this therapeutic strategy is limited by the inevitable disease progression to androgen-independence associated with enrichment of a propagating androgen-independent cell population resistant to apoptosis, making treatment of advanced stage disease more difficult. One approach for treatment of androgen-independent prostate cancer involves targeting pro-apoptotic proteins, such as Bax, in the prostate epithelia. Bax is a latent apoptotic protein that normally localizes to the cytosol, or loosely associates with intracellular membranes. Upon receiving apoptotic stimuli, Bax targets and integrates into the mitochondrial and/or ER membrane where it induces opening of the permeability transition pore and perturbation of intracellular Ca homeostasis, leading to activation of the downstream caspase pathways. Although adenovirus-mediated over-expression of Bax has been demonstrated to induce apoptosis in prostate cancer cells, and to effectively reduce tumor size in nude mice, the response of experimental prostate tumors to Bax over-expression is short-lived, with most tumors relapsing regardless of viral inoculums. The characteristic of prostate cancer relapse following Bax treatment indicates that adaptive changes in cellular machinery may account for the sustained elevation of Bax and the metastatic nature of tumor cells.

It has been suggested that down-regulation of SOCE may be a general phenomenon during progression to androgen-resistant prostate cancer. Bcl-2 over-expression in LNCaP prostate cancer cells could transform these cells from an androgen dependent to an androgen independent phenotype via reduced function of SOCE. Neuroendocrine differentiation of LNCaP cells, which leads to a cessation of cell proliferative activity, and confers apoptotic resistance via a Bcl-2-independent mechanism, also results in reduced SOCE. Over-expression of Bax causes a loss of ER Ca content presumably via Bax-mediated changes in ion-permeability of the ER membrane; and, release of Ca from the ER store enhances the partition of Bax into the mitochondrial membrane, synergizing apoptosis signaling.

It has been reported that NRP-154, an androgen-independent tumorigenic prostate epithelial cell line, can sustain high level expression of exogenous Bax (Lin, P. H. et al. 2005. *Cell Res.* 15:160-166). This is in contrast to results seen in non-tumor cells, where Bax has been described as a ubiquitous stimulator of cell death. These data indicated that other adaptive factors may exist in NRP-154 cells to antagonize the apoptotic effect of latent Bax in the cytosol.

Experiments were performed with NRP-154 cells with stable over-expression of Bax. The relationship between Bax and Ca in apoptosis signaling was examined. One of the compensatory changes in NRP-154 cells with sustained Bax over-expression that was identified was the significant down-regulation of SOCE. NRP-154 cells that over-expressed Bax displayed increased sensitivity to TGF-β and Ca-induced apoptosis, events that are closely related to the level of SOCE activation. These data provided evidence that Bax acts synergistically with Ca in apoptosis signaling, and indicated that combination of Bax over-expression with activation of SOCE may provide an effective strategy for the therapeutic intervention of prostate cancer.

Figure 14A:
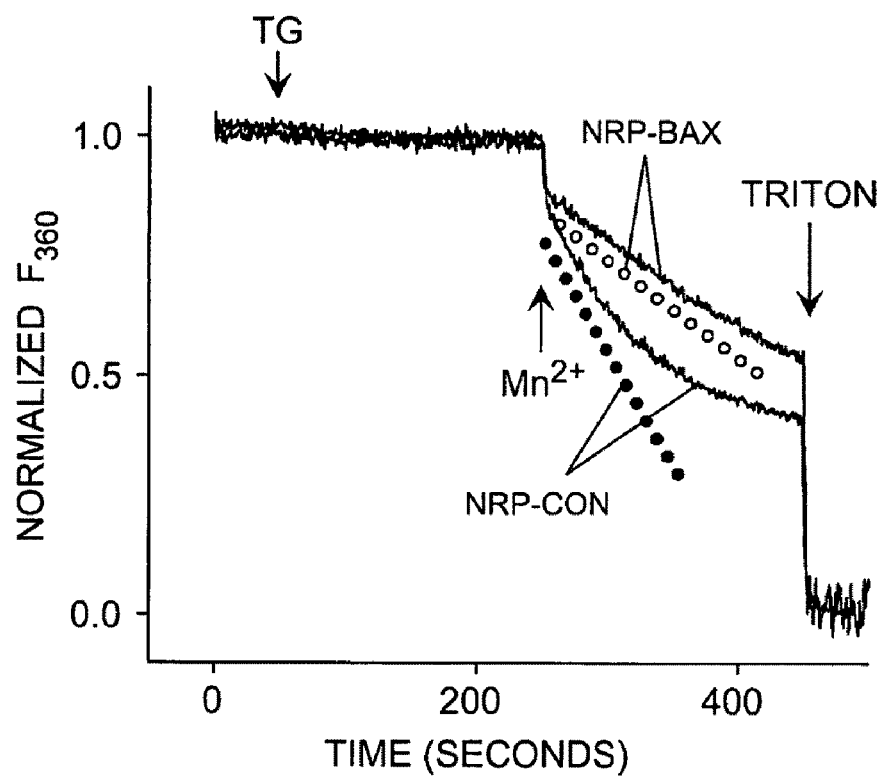
FIG. 14A shows results where NRP-Con and NRP-Bax cells were loaded with 5 μM Fura-2 AM, and their ER Ca storage was depleted with the addition of 10 4M thapsigargin (TG). Addition of 0.5 mM $Mn^{2+}$ led to quenching of Fura-2 fluorescence measured at an excitation wavelength of 360 nm. A significantly slower rate of Mn-quenching of Fura-2 was observed in NRP-Bax cells.
Figure 14B:
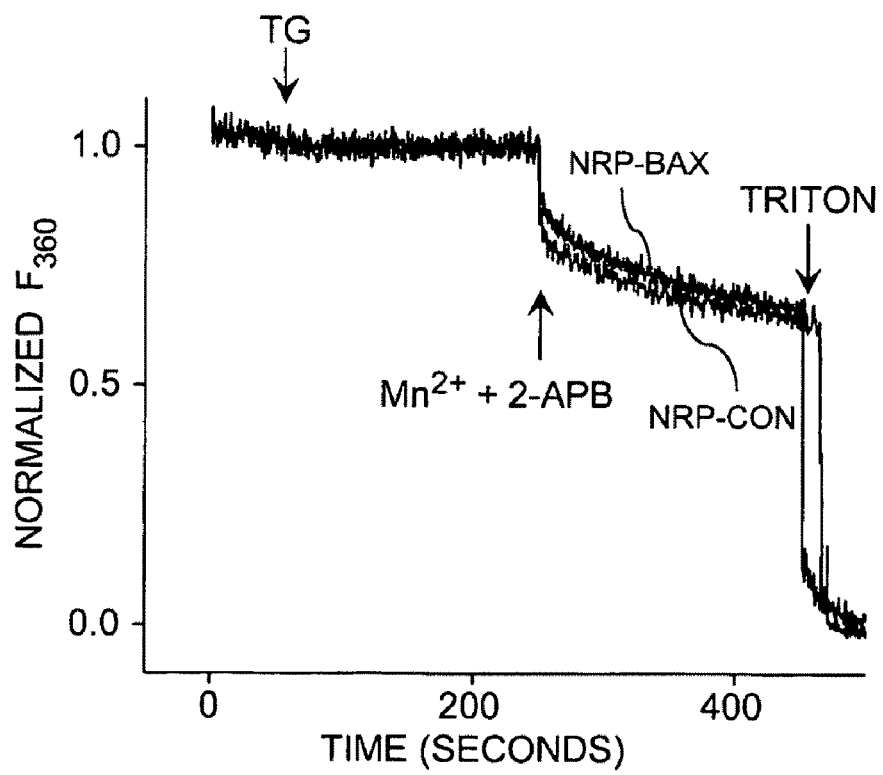
FIG. 14B depicts results where addition of 10 μM 2-APB to the $Mn^{2+}$-solution inhibited SOCE in both NRP-Con and NRP-Bax cells, and blunted the difference in Mn-quenching of Fura-2 fluorescence between these two cell lines (n=6 for NRP-Con, and n=5 for NRP-Bax).

The role of SOCE in Ca signaling in NRP-154 cells was examined. First, 10 μM thapsigargin, a potent inhibitor of SERCA, was applied to cells in an extracellular solution without Ca to allow for passive depletion of the ER Ca stores. Following ER Ca depletion (200 s treatment), 0.5 mM $MnCl_2$ was added into cuvettes containing $1 \times 10^6$ NRP-154 cells loaded with Fura-2. The quenching of Fura-2 fluorescence by the entry of $Mn^{2+}$ provided a quantitative assay of SOCE. Specifically, the slope of reduction of Fura-2 fluorescence with time reflected the degree of SOCE activation. As shown in FIG. 14A, the rate of Fura-2 quenching by $Mn^{2+}$ was significantly slower in NRP-Bax cells compared to NRP-Con cells. The difference in $Mn^{2+}$-induced quenching of Fura-2 fluorescence could be abolished by pre-incubation of the cells with 10 μM 2-APB, a known SOCE antagonist (see FIG. 14B).

Figure 14C:
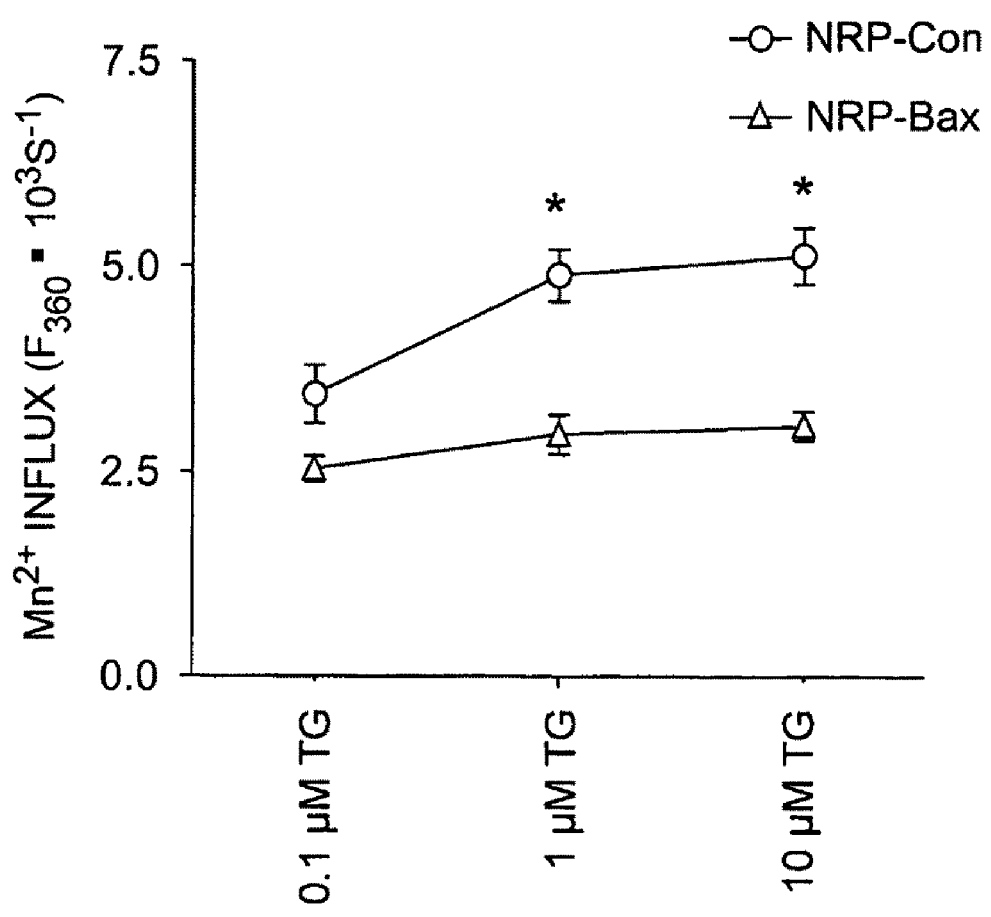
FIG. 14C shows the dose-dependent activation of TG-induced SOCE in NRP-Con and NRP-Bax cells. The concentrations of TG tested were: 0.1 μM (n=7 for both cell lines, p=0.04); 1 μM (n=7 for both cell lines, p<0.01); 10 μM (n=8 for both cell lines, p<0.01).

By varying the concentration of thapsigargin, the dose-dependency of TG on SOCE activation in NRP-Con and NRP-Bax cells was determined (see FIG. 14C). At a concentration of 0.1 μM thapsigargin, the difference in SOCE activation between the NRP-Con and NRP-Bax cells was significantly less than those observed at higher thapsigargin concentrations. These data demonstrated that reduced SOCE represents a compensatory response of NRP-154 cells to sustained over-expression of Bax, which leads to reduced ER Ca stores and reduced resting Ca in the cytosol. Therefore application of an agent such as P311 to prostate cancer cells, an agent that modulates activity of SOCE, would be predicted to induce the death of such cancer cells (apoptosis) and thus provide a therapeutic benefit for patients.

In any of the applications described for the P311 protein as a therapeutic agent, it may be necessary to enhance delivery of the P311 protein. Therefore, particular embodiments of the present invention involve fusing the P311 protein to a cell penetrating moiety (e.g., a protein transduction domain). As used herein, a cell penetrating moiety is any molecule which can be operably attached to the P311 protein of the present invention to facilitate, enhance, or increase the transport of said protein into target tissue. Such a moiety can be a protein, peptide or small molecule. For example, a variety of protein transduction domains, including the HIV-1 TAT transcription factor, *Drosophila* Antennapedia transcription factor, as well as the herpes simplex virus VP22 protein have been shown to facilitate transport of proteins into the cell (Wadia and Dowdy. 2002. *Curr. Opin. Biotechnol.* 13:52-56). Further, an arginine-rich peptide (Futaki. 2002 *Int. J. Pharm.* 245:1-7), a polylysine peptide containing Tat PTD (Hashida, et al. 2004. *Br. J. Cancer* 90(6):1252-8), Pep-1 (Deshayes, et al. 2004. *Biochemistry* 43(6):1449-57) or an HSP70 protein or fragment thereof (WO 00/31113) is suitable for use with the present invention. Not to be bound by theory, it is believed that such transport domains are highly basic and appear to interact strongly with the plasma membrane and subsequently enter cells via endocytosis (Wadia, et al. 2004. *Nat. Med.* 10:310-315).

Exemplary peptide-based cell penetrating moieties are presented in Table 1.

TABLE 1

| SOURCE | AMINO ACID SEQUENCE | SEQ ID NO: |
|---|---|---|
| HIV TAT[a] | YGRKKRRQRRR | 2 |
| PTD-4[a] | YARAAARQARA | 3 |
| PTD-3[a] | GRKKRRQRRR | 4 |
| PTD-5[a] | YARKARRQARR | 5 |
| PTD-6[a] | YARAARRAARR | 6 |
| PTD-7[a] | YARAARRAARA | 7 |
| ANTp[b] | YARRRRRRRRR | 8 |
| Transportin[b] | RQIKIWFQNRRMKWKK GWTLNSAGYLLGKINLKALAALAKKIL | 9 |

[a]Ho, et al. (2001) Cancer Res. 61: 474-477.
[b]Schwartz and Zhang (2000) Curr. Opin. Mol. Ther. 2:2.

Suitable small molecules cell penetrating moieties which can be operably attached to the P311 protein of the present invention include, but are not limited to, nonpeptidic polyguanidylated dendritic structures (Chung, et al. 2004. *Biopolymers* 76(1):83-96) or poly[N-(2-hydroxypropyl) methacrylamide] (Christie, et al. 2004. *Biomed. Sci. Instrum.* 40:136-41).

In a preferred embodiment, P311 (SEQ ID NO: 1 or SEQ ID NO: 10) is used to treat disease. The diseases encompassed by the present invention include diseases where alterations in the activity of SOCE are integral to disease pathogenesis, and thus are desired targets for disease prevention and/or treatment. The specific diseases contemplated would include but not be limited to dental diseases such as gingivitis, muscle aging, and cancer, in particular prostate cancer. To optimize the activity of P311 as a modulator of SOCE activity in vivo, the P311 peptide sequence will be fused in a preferred embodiment to a cell penetrating peptide. This will allow application of the P311-fusion peptide to target tissues and cells through a number of means. For example, the P311-fusion peptide can be added to or formulated in a form targeted to the desired treatment need. For treatment of gingivitis, the P311 could be formulated as toothpaste or any other dental vector that will allow for targeting cells of interest in the gum or gingival area without affecting other cellular systems where P311 might have unwanted effects. For treatment of other diseases, the P311 could be formulated in an oral solution, a dietary supplement, a food, a capsule, a gel, an ointment, any type of topical formulation, an injectable solution, or any other vector appropriate for delivering the peptide to the tissue to be targeted. The presence of cell-penetrating peptide will permit entry into nearly any mammalian cell type and allow P311 to elevate SOCE in the target cells. Recombinant P311-TAT has been cloned and expressed in bacteria. Full-length P311 has been solubilized and prepared in a form useful for formulation and the P311 fusion protein should be soluble as well.

Based on its identified properties, P311 has numerous potential applications in medicine, including dental healthcare. Through fusion with the cell-penetrating peptide tag, P311 can be used to elevate SOCE in cells using various established methods of application, methods known to one of skill in the art. Since the P311-cell-penetrating peptide fusion protein simply has to be placed on the target cells to be effective, it can be used as a supplement in numerous products to improve dental health. In particular for dental health products, other dental products, such as dental adhesives, adhesive strips and orthodontics could be supplemented with P311-fusion protein to apply the peptide for extended periods. By elevating SOCE in response to bacterial challenges, the health status of cells of the mouth and gum lining will be improved and the pathological effects of gingivitis and other dental diseases will be prevented.

Also contemplated by the present invention are other potential uses of P311. P311 could be used to treat any disease or disorder where decreased SOCE activity is involved in the pathogenesis. Examples of uses of the P311 include treatment of skin disorders since P311 can be applied topically. Methods for optimizing the biological activity of P311 are also being developed as a way to enhance the short half-life of the protein in vivo. It is known that P311 has a rapid turnover time in the cell that is related at least in part to ubiquitin-mediated degradation. Mutation of such target sites in the P311 sequence may prolong the effectiveness of a single treatment with P311 by extending the half-life of the peptide inside the cell.

The present invention, therefore, includes compositions for prevention and treatment of diseases in animals, including humans, which comprise an isolated and purified P311 protein (SEQ ID NO: 1 or SEQ ID NO: 10) fused to a cell penetrating peptide and a pharmaceutically acceptable vehicle. In a preferred embodiment, the disease being treated or prevented is gingivitis, aging muscle, or cancer. The present invention is also a composition for increasing store-operated calcium entry in a cell which comprises an isolated and purified P311 protein (SEQ ID NO: 1 or SEQ ID NO: 10) fused to a cell penetrating peptide and a pharmaceutically acceptable vehicle. Also contemplated by the present invention are compositions for improving dental health in an animal which comprise an isolated and purified P311 protein (SEQ ID NO: 1 or SEQ ID NO: 10) fused to a cell penetrating peptide and a pharmaceutically acceptable vehicle. In addition to the compositions of the present invention, several methods are also provided. The basic method of the present invention is a method for increasing store-operated calcium entry in a cell which comprises contacting said cell with the composition which comprises an isolated and purified P311 protein (SEQ ID NO: 1 or SEQ ID NO: 10) fused to a cell penetrating peptide and a pharmaceutically acceptable vehicle, wherein contact of said cell with said composition results in an increase in the level of store-operated calcium entry in the cell.

Other methods of the present invention are methods for preventing and/or treating disease in an animal which comprise administering to said animal a therapeutically effective amount of the composition which comprises an isolated and purified P311 protein (SEQ ID NO: 1 or SEQ ID NO: 10) fused to a cell penetrating peptide and a pharmaceutically acceptable vehicle, wherein administration of said composition to said animal results in prevention or treatment of disease. In preferred embodiments the diseases are gingivitis, aging muscle, or prostate cancer.

Finally, also included in the present invention are compositions and methods for disease treatment, wherein the disease involves alterations in SOCE, and further wherein the compositions include mutated or variant P311 proteins. Modifications of the P311 protein that are contemplated include but are not limited to site-specific mutations or chemical cross-linking, or any such modification of the P311 protein that would alter the ability of P311 to regulate SOCE. Such modifications of the P311 protein are commonly employed by those of skill in the art to affect function of proteins.

In order to make and use the compositions and methods of the present invention, one of skill would use well-accepted methods in drug formulation and oral care product formulation to develop and optimize compositions that would used to prevent and treat disease.

The following non-limiting examples are provided to further illustrate the present invention.

EXAMPLES

Example 1

Cell Culture Methods

Human embryonic palate mesenchymal (HEPM) cells, a cell line derived from the soft palate of a human fetus, were maintained in Dulbecco's Modified Eagle Media with 10% fetal bovine serum (FBS), 1% penicillin and streptomycin. Cells were cultured until 90% confluent and then either split into additional culture vessels or used for experimentation.

Chinese hamster ovary (CHO) cells were maintained in Ham's F-12 medium supplemented with 10% fetal bovine serum (FBS), 1% penicillin and streptomycin. Culture of C2C12 myogenic cells was described previously (Shin, D. W. et al. 2002. Biophys. J. 83:2539-2549). Myotubes derived from C2C12 were used in experiments at day 5 of differentiation.

Example 2

Intracellular Ca Measurements

HEPM cells were loaded with 10 µM Fura-2 AM (Invitrogen, Carlsbad, Calif.) for 45 min at 37° C. and allowed to de-esterify for 15 min at 25° C. Cells were then harvested and re-suspended in balanced salt solution (BSS) containing (in mM): 140 NaCl, 2.8 KCl, 2 $CaCl_2$, 2 $MgCl_2$, 10 HEPES, pH 7.2. $2.5 \times 10^6$ cells were transferred into the cuvette system of a PTI spectrofluorometer (Photon Technology International, Princeton, N.J.) and the changes in $[Ca]_i$ were measured as changes in the ratio of Fura-2 fluorescence at excitation wavelength of 350 nm ($F_{350}$) and 380 nm ($F_{380}$), following exposure to various concentrations of thapsigargin, ionomycin or caffeine and ryanodine (C/R). For measurement in 0.5 mM EGTA, cells were centrifuged and re-suspended in BSS without $CaCl_2$, and 0.5 mM EGTA was added immediately before recordings. Measurement of Ca in individual C2C12 myotubes were performed as described before (Shin, D. W. et al. 2003. J. Biol. Chem. 278:3286-3292). All experiments were conducted at 25±2° C.

Example 3

SOCE Determination by Mn Quenching of Fura-2

Manganese ($Mn^{2+}$) is known to be able to permeate into cells via store-operated Ca channels (SOCs), but is impervious to surface membrane extrusion processes or SR uptake by Ca pumps. Hence, $Mn^{2+}$ fluorescence quenching represents a measurement of unidirectional Ca flux into cells via SOC (Shin, D. W. et al. 2003. J. Biol. Chem. 278:3286-3292; Pan, Z. et al. 2002. Nat. Cell. Biol. 4:379-383). Briefly, to measure the $Mn^{2+}$ influx rate through the SOC machinery, thapsigargin (TG), or C/R, was applied to cultured cells or C2C12 myotubes to induce SR Ca depletion in 0 mM extracellular CaCa ($[CaCa]_o$), then 0.5 mM $Mn^{2+}$ was added to the extracellular solution. The quenching of Fura-2 fluorescence by $Mn^{2+}$ was measured at the Ca-independent excitation wavelength of Fura-2 (360 nm). The decay of Fura-2 fluorescence upon $Mn^{2+}$ addition was expressed as percent decrease in Fura-2 fluorescence per unit time (the initial fluorescence is set equal to 100%). For all measurements of SOCE by $Mn^{2+}$ quenching, the maximally quenched fluorescence signal was established at the end of the experiment by lysing the cells with 1% Triton, and set equal to 0% fluorescence.

Example 4

SOCE Measurement by Mn Entry in Muscle Fibers

Preparation methods of Flexor Digitorum Brevis (FDB) muscle fibers has been described elsewhere (Wang, X. et al. 2005. Nat. Cell. Biol. 7:525-530). Briefly, individual FDB muscle fibers from C57B16/J wild-type male mice were enzymatically disassociated by 2 mg/ml Type I collagenase (Sigma, St. Louis, Mo.) and plated onto ΔTC dish (Bioptechs, Inc., Butler, Pa.). Fibers were allowed to attach to the bottom of the dish and loaded with 10 µM Fura-2 AM (Molecular Probes, Eugene, Oreg.) at room temperature for 1 hour. To prevent motion artifact in muscle fibers, 20 µM N-benzyl-p-toluene sulphonamide (BTS) (Sigma, St. Louis, Mo.), a specific myosin II inhibitor was applied into the bathing solution 15 min prior to induction of SR Ca depletion. Muscle fibers were then examined on the inverted microscopy (400× magnification, N.A. 1.3) of a PTI spectrofluorometer system (Photon Technology International, Monmouth Junction, N.J.). Fura-2 was excited at 360 nm, a wavelength insensitive to changes in $[Ca]_i$, while emission at wavelength of 510 nm was recorded. To deplete SR Ca store, FDB fibers were treated with 20 mM caffeine plus 5 µM ryanodine (C/R) for 5 min to induce Ca release. The perfusion solution was then switched to 0.5 mM $Mn^{2+}$ for 5 min to observe the extent of $Mn^{2+}$ entry and establish the rate of SOCE. For all measurements of SOCE by $Mn^{2+}$ quenching the florescence signal was normalized using values determined by lysis of the cells with 1% Triton at the end of the experiment. All experiments were conducted at room temperature.

Example 5

Isolation of Recombinant P311

Using standard recombinant DNA technology, the full-length P311 protein was cloned into a T7-based expression plasmid with a 6× His-tag at either the amino-terminus (pET15b, Novagen) or the carboxy-terminus (pET21b, Novagen) and as a fusion protein with glutathione S-transferase (GST) in plasmid pGEX-2T (Pharmacia). In addition, the untagged P311 was cloned into a T7-based bacterial expression vector pG5 (Alexander, P. et al. 1992. Biochemistry 31:3597-3603). The bacterial host is grown for 12-14 hours at room temperature or for 4 hours at 37° C. after induction with 0.2 mM IPTG. Robust expression for the amino-terminal His6-tagged P311 protein A portion of the overexpressed was observed; the amino-terminal His6-tagged P311 protein was soluble. The soluble fraction of the His6-tagged P311 protein in the E. coli lysate was purified over a Ni-NTA agarose column. The protein was eluted by 250 mM immidazole and further purified by anion-exchange chromatography (Source-15S, Pharmacia) and gel-filtration chromatography (Superdex-200, Pharmacia). The P311 protein was purified to greater than 80% homogeneity as judged on SDS-PAGE. The concentration of P311 was determined by spectroscopic measurement at 280 nm.

Example 6

Measurement of $I_{CRAC}$

Jurkat cells were cultured using standard techniques. For electrophysiology, the bathing solution contained (in mM)— 160 NaCl, 5 KCl, 2 MgCl2, 10 glucose, 10 HEPES, and either 0, 2, or 20 $CaCl_2$ (pH=7.2) Pipette solution contained (in mM)—140 Cs-aspartate, 3 MgCl2, 10 EGTA, and 10 HEPES. (pH=7.4) Pipettes were fabricated from borosilicate glass using a Flaming/Brown microelectrode puller and fire polished to a resistance of 2-5 MΩ when filled with pipette solution. Stimulation and data acquisition were performed using an Axopatch 200B interfaced to pClamp 8.2 software. Currents were filtered at 1 kHz and digitized at 5 kHz. Cells with similar size were used for the current measurements. The standard whole-cell configuration was used to measure the $I_{CRAC}$ current. A ramp test pulse protocol (100 ms duration, ranging from −130 mV to +30 mV) was applied every 2 s.

Upon establishment of the whole-cell configuration, cells were perfused with Ca-free solution containing 2 μM thapsigargin, allowing passive depletion of the ER Ca store and activation of $I_{CRAC}$. After ~3 minutes, extracellular Ca was raised to 20 mM in order to monitor Ca flux through CRAC channels. Averaged leak current observed in the Ca-free condition was subtracted from the test current obtained in the presence of 20 mM external Ca in order to isolate $I_{CRAC}$.

What is claimed is:

1. A composition for increasing store-operated calcium entry in a cell comprising
   (a) an isolated and purified P311 protein fused to a cell penetrating peptide, and
   (b) a pharmaceutically acceptable vehicle,
wherein said composition is formulated as toothpaste, a dental rinse, or a food supplement.

2. A method for increasing store-operated calcium entry in a cell comprising contacting a cell with a composition comprising
   (a) an isolated and purified P311 protein fused to a cell penetrating peptide, and
   (b) a pharmaceutically acceptable vehicle,
wherein contact of said cell with said composition results in an increase in the level of store-operated calcium entry in the cell.

3. The method of claim 2, wherein said cell is a mammalian gingival cell, a skeletal muscle cell, or a prostate epithelial cell.

4. A method for preventing or treating dental disease in an animal comprising administering to an animal a therapeutically effective amount of a composition comprising
   (a) an isolated and purified P311 protein fused to a cell penetrating peptide, and
   (b) a pharmaceutically acceptable vehicle,
wherein administration of said composition to said animal results in prevention or treatment of dental disease.

5. The method of claim 4, wherein said dental disease is gingivitis.

6. The method of claim 4, wherein said composition is formulated as toothpaste, a dental rinse, or a food supplement.

7. A method for treating prostate cancer in an animal comprising administering to an animal with prostate cancer a therapeutically effective amount of a composition comprising
   (a) an isolated and purified P311 protein fused to a cell penetrating peptide, and
   (b) a pharmaceutically acceptable vehicle,
wherein administration of said composition to said animal results in treatment of prostate cancer.

* * * * *

SEQUENCE LISTING

```
<160> NUMBER OF SEQ ID NOS: 11

<210> SEQ ID NO 1
<211> LENGTH: 68
<212> TYPE: PRT
<213> ORGANISM: Homo sapiens

<400> SEQUENCE: 1

Met Val Tyr Tyr Pro Glu Leu Phe Val Trp Val Ser Gln Glu Pro Phe
1               5                   10                  15

Pro Asn Lys Asp Met Glu Gly Arg Leu Pro Lys Gly Arg Leu Pro Val
            20                  25                  30

Pro Lys Glu Val Asn Arg Lys Lys Asn Asp Glu Thr Asn Ala Ala Ser
        35                  40                  45

Leu Thr Pro Leu Gly Ser Ser Glu Leu Arg Ser Pro Arg Ile Ser Tyr
    50                  55                  60

Leu His Phe Phe
65

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Tyr Gly Arg Lys Lys Arg Arg Gln Arg Arg Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide

<400> SEQUENCE: 3

Tyr Ala Arg Ala Ala Ala Arg Gln Ala Arg Ala
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide

<400> SEQUENCE: 4

Tyr Ala Arg Lys Ala Arg Arg Gln Ala Arg Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide
```

```
<400> SEQUENCE: 5

Tyr Ala Arg Ala Ala Arg Arg Ala Ala Arg Arg
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide

<400> SEQUENCE: 6

Tyr Ala Arg Ala Ala Arg Arg Ala Ala Arg Ala
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

<400> SEQUENCE: 7

Tyr Ala Arg Arg Arg Arg Arg Arg Arg Arg Arg
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 27
<212> TYPE: PRT
<213> ORGANISM: Artificial Sequence
<220> FEATURE:
<223> OTHER INFORMATION: Synthetic peptide

<400> SEQUENCE: 9

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 10
<211> LENGTH: 68
<212> TYPE: PRT
<213> ORGANISM: Mus musculus

<400> SEQUENCE: 10

Met Val Tyr Tyr Pro Glu Leu Leu Val Trp Val Ser Gln Glu Pro Phe
1               5                   10                  15

Ala Tyr Lys Glu Met Glu Gly Gly Leu Ile Lys Gly Arg Leu Pro Val
            20                  25                  30

Pro Lys Glu Val Asn Arg Lys Lys Met Glu Glu Thr Gly Ala Ala Ser
        35                  40                  45
```

-continued

```
Leu Thr Pro Pro Gly Ser Arg Glu Phe Thr Ser Pro Ala Thr Ser Tyr
    50                  55                  60

Leu His Pro Phe
65

<210> SEQ ID NO 11
<211> LENGTH: 66
<212> TYPE: PRT
<213> ORGANISM: Caenorhabditis elegans

<400> SEQUENCE: 11

His Arg Ile Ile Pro Asn Phe Met Ile Gln Gly Gly Asp Phe Thr Arg
1               5                   10                  15

Gly Asn Gly Thr Gly Gly Glu Ser Ile Tyr Gly Glu Lys Phe Pro Asp
                20                  25                  30

Glu Asn Phe Lys Glu Lys His Thr Gly Pro Gly Val Leu Ser Met Ala
            35                  40                  45

Asn Ala Gly Pro Asn Thr Asn Gly Ser Gln Phe Phe Leu Cys Thr Val
    50                  55                  60

Lys Thr
65
```